US010246231B2

(12) United States Patent
Crawford

(10) Patent No.: US 10,246,231 B2
(45) Date of Patent: Apr. 2, 2019

(54) CONTAINER

(71) Applicant: COLGATE-PALMOLIVE COMPANY, New York, NY (US)

(72) Inventor: John Crawford, Mahopac, NY (US)

(73) Assignee: Colgate-Palmolive Company, New York, NY (US)

(*) Notice: Subject to any disclaimer, the term of this patent is extended or adjusted under 35 U.S.C. 154(b) by 107 days.

(21) Appl. No.: 15/125,458

(22) PCT Filed: Mar. 12, 2014

(86) PCT No.: PCT/US2014/024553
§ 371 (c)(1),
(2) Date: Sep. 12, 2016

(87) PCT Pub. No.: WO2015/137941
PCT Pub. Date: Sep. 17, 2015

(65) Prior Publication Data
US 2017/0073131 A1 Mar. 16, 2017

(51) Int. Cl.
*A61L 9/04* (2006.01)
*B65D 51/24* (2006.01)
*A61L 9/12* (2006.01)
*B65D 25/42* (2006.01)
*A45D 34/00* (2006.01)
*A61L 9/014* (2006.01)

(52) U.S. Cl.
CPC ............ *B65D 51/24* (2013.01); *A45D 34/00* (2013.01); *A61L 9/014* (2013.01); *A61L 9/04* (2013.01);
(Continued)

(58) Field of Classification Search
CPC ........ B65D 51/24; B65D 25/42; A45D 34/00; A61L 9/04; A61L 9/12
(Continued)

(56) References Cited

U.S. PATENT DOCUMENTS 4,858,758 A 8/1989 Mitchell
6,769,631 B2 * 8/2004 Brown ................ A61L 9/12
222/192
(Continued)

FOREIGN PATENT DOCUMENTS

DE 20 2005 002986 6/2005
JP H02139362 5/1990
(Continued)

OTHER PUBLICATIONS

International Search Report and the Written Opinion of the International Searching Authority issued in International Application PCT/US2014/024553 dated May 27, 2014.

*Primary Examiner* — Steven J Ganey

(57) ABSTRACT

Disclosed is a container comprising a vessel defining a chamber storing a volume of a flowable substance having a fragrance, such as a personal care or a home care product; a body defining an opening through which the flowable substance is dispensable from the chamber; and a porous element for retaining a quantity of the flowable substance, the porous element being at a position relative to the volume of the flowable substance so that the flowable substance comes into contact with the porous element as a result of the flowable substance being dispensed from the chamber through the opening. The porous element may be comprised in the body or in a closure that is movable relative to the body between a first position, at which the closure isolates the opening from an exterior of the container, and a second position at which the opening is not isolated from the exterior.

13 Claims, 15 Drawing Sheets

(52) U.S. Cl.
CPC ............... *A61L 9/12* (2013.01); *B65D 25/42* (2013.01); *A45D 2034/002* (2013.01); *A61L 9/127* (2013.01)

(58) Field of Classification Search
USPC ... 239/34, 37, 42–44, 47, 55, 289, 326, 327, 239/328; 222/95, 192, 211
See application file for complete search history.

(56) References Cited

U.S. PATENT DOCUMENTS

| | | | |
|---|---|---|---|
| 6,945,473 B2* | 9/2005 | Garcia | A61L 9/12 239/326 |
| 7,681,809 B2* | 3/2010 | Maget | A01M 1/2044 239/34 |
| 2002/0139093 A1 | 10/2002 | Landau | |
| 2006/0175349 A1 | 8/2006 | Drosos | |
| 2006/0283888 A1 | 12/2006 | Kinscherf | |
| 2008/0237248 A1 | 10/2008 | Dente | |
| 2008/0277373 A1 | 11/2008 | Gibis | |
| 2008/0286143 A1 | 11/2008 | Grodsky | |
| 2010/0264169 A1 | 10/2010 | Crawford | |

FOREIGN PATENT DOCUMENTS

| | | |
|---|---|---|
| JP | 2000085777 | 3/2000 |
| KR | 20030070696 | 9/2003 |
| WO | WO 2001/023274 | 4/2001 |
| WO | WO 2013/192428 | 12/2013 |

\* cited by examiner

CONTAINER

BACKGROUND

The present invention relates to a container, such as a bottle, for storing a flowable substance, such as a personal care product or a home care product, which has a fragrance.

There are various known containers, each with a chamber for storing a flowable substance having a fragrance, an opening through which the flowable substance is dispensable from the chamber, and a closure for selectively closing the opening. However, when a user removes or opens the closure of such a container and sniffs to determine the fragrance of the flowable substance in the chamber, delivery of the fragrance of the flowable substance to the user is limited. Some known such containers have connected thereto an additional substance with a fragrance supposedly matching that of the flowable substance within the chamber of the container. A user may sniff the additional substance prior to purchase or use of the container to get an idea of the fragrance of the flowable substance. However, often the fragrance of the additional substance does not match that of the flowable substance within the chamber of the container.

There is a need for a container comprising an improved system for delivering to a user a fragrance of a flowable substance in a chamber of a container.

BRIEF SUMMARY

A first embodiment of the present invention provides a container defining a chamber storing a volume of a flowable substance having a fragrance and defining an opening through which the flowable substance is dispensable from the chamber; the container comprising a porous element for retaining a quantity of the flowable substance, the porous element being at a position relative to the volume of the flowable substance so that the flowable substance comes into contact with the porous element as a result of the flowable substance being dispensed from the chamber through the opening.

Optionally, the porous element is at a position relative to the volume of the flowable substance so that the flowable substance comes into contact with the porous element as the flowable substance is dispensed from the chamber through the opening.

Optionally, the container comprises a vessel defining the chamber; a body defining the opening; and a closure movable relative to the vessel between a first position at which the closure isolates the opening from an exterior of the container and a second position at which the opening is not isolated from the exterior of the container by the closure, the closure comprising the porous element.

Optionally, the container comprises a vessel defining the chamber; and a body defining the opening, the body comprising the porous element.

A second embodiment of the present invention provides a container, comprising: a vessel defining a chamber for storing a volume of a flowable substance having a fragrance; and a body defining an opening through which the flowable substance is dispensable from the chamber, the body comprising a porous element for retaining a quantity of the flowable substance.

Optionally, in either of the containers of the first and second embodiments, the opening is partially or fully defined by the porous element.

Optionally, in either of the containers of the first and second embodiments, the body comprises a member and the porous element is affixed to the member. Further optionally, the opening is partially or fully defined by the member. Optionally, the porous element comprises a liner affixed to the member.

Optionally, in either of the containers of the first and second embodiments, the porous element partially or fully surrounds the opening.

Optionally, either of the containers of the first and second embodiments comprises a closure movable relative to the vessel between a first position at which the closure isolates the opening from an exterior of the container and a second position at which the opening is not isolated from the exterior of the container by the closure.

A third embodiment of the present invention provides a container, comprising: a vessel defining a chamber for storing a volume of a flowable substance having a fragrance; a body defining an opening through which the flowable substance is dispensable from the chamber; and a closure movable relative to the vessel between a first position at which the closure isolates the opening from an exterior of the container and a second position at which the opening is not isolated from the exterior of the container by the closure, the closure comprising a porous element for retaining a quantity of the flowable substance.

Optionally, in either of the containers of the first and third embodiments, the closure comprises a closure member, and the porous element is affixed to the closure member or is unitary with the closure member. Further optionally, the closure is movable relative to the vessel between the first position at which at least a portion of the porous member is in the opening and the second position at which none of the porous element is in the opening.

Optionally, in any of the containers of the first to third embodiments, the porous element forms a seal isolating an interior of the closure from an exterior of the container when the closure is at the first position relative to the vessel. Further optionally, the porous element is compressed between the closure and one of the body and the vessel when the closure is at the first position relative to the vessel.

Optionally, in any of the containers of the first to third embodiments, the porous element is in fluid communication with the chamber when the closure is at the first position relative to the vessel.

Optionally, in any of the containers of the first to third embodiments, the porous element is isolated from the chamber when the closure is at the first position, and the porous element is in fluid communication with the chamber when the closure is at the second position.

Optionally, in any of the containers of the first to third embodiments, the porous element is isolated from an exterior of the container when the closure is at the first position, and the porous element is in fluid communication with the exterior of the container when the closure is at the second position.

Optionally, in any of the containers of the first to third embodiments, the porous element partially or fully surrounds the body when the closure is at the first position.

Optionally, in any of the containers of the first to third embodiments, one or more apertures extend through the closure, each of the one or more apertures being in fluid communication with the porous element when the closure is at the first position relative to the vessel. Further optionally, the container comprises a seal on the exterior of the closure, wherein the seal is movable relative to the closure between a first position at which the seal isolates the, or each, of the one or more apertures from an exterior of the container and a second position at which the seal does not isolate the, or each, of the one or more apertures from the exterior of the container.

Optionally, in any of the containers of the first to third embodiments, the body is affixed to the vessel.

Optionally, in any of the containers of the first to third embodiments, the body is unitary with the vessel.

Optionally, in any of the containers of the first to third embodiments, the opening is defined by a spout.

Optionally, in any of the containers of the first to third embodiments, the porous element is absorbent.

Optionally, in any of the containers of the first to third embodiments, the porous element comprises one or more of a wick, sintered plastic, pulp material, screen material, and pressed paperboard.

Optionally, in any of the containers of the first to third embodiments, the flowable substance is one of a personal care product and a home care product. Further optionally, the personal care product is one of a hand soap, a dentifrice, a hair care product, a body wash, and a mouthwash. Further optionally, the home care product is one of a laundry detergent, a dish washing detergent, a fabric softener, a fabric conditioner, a floor cleaner, and a surface cleaner.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
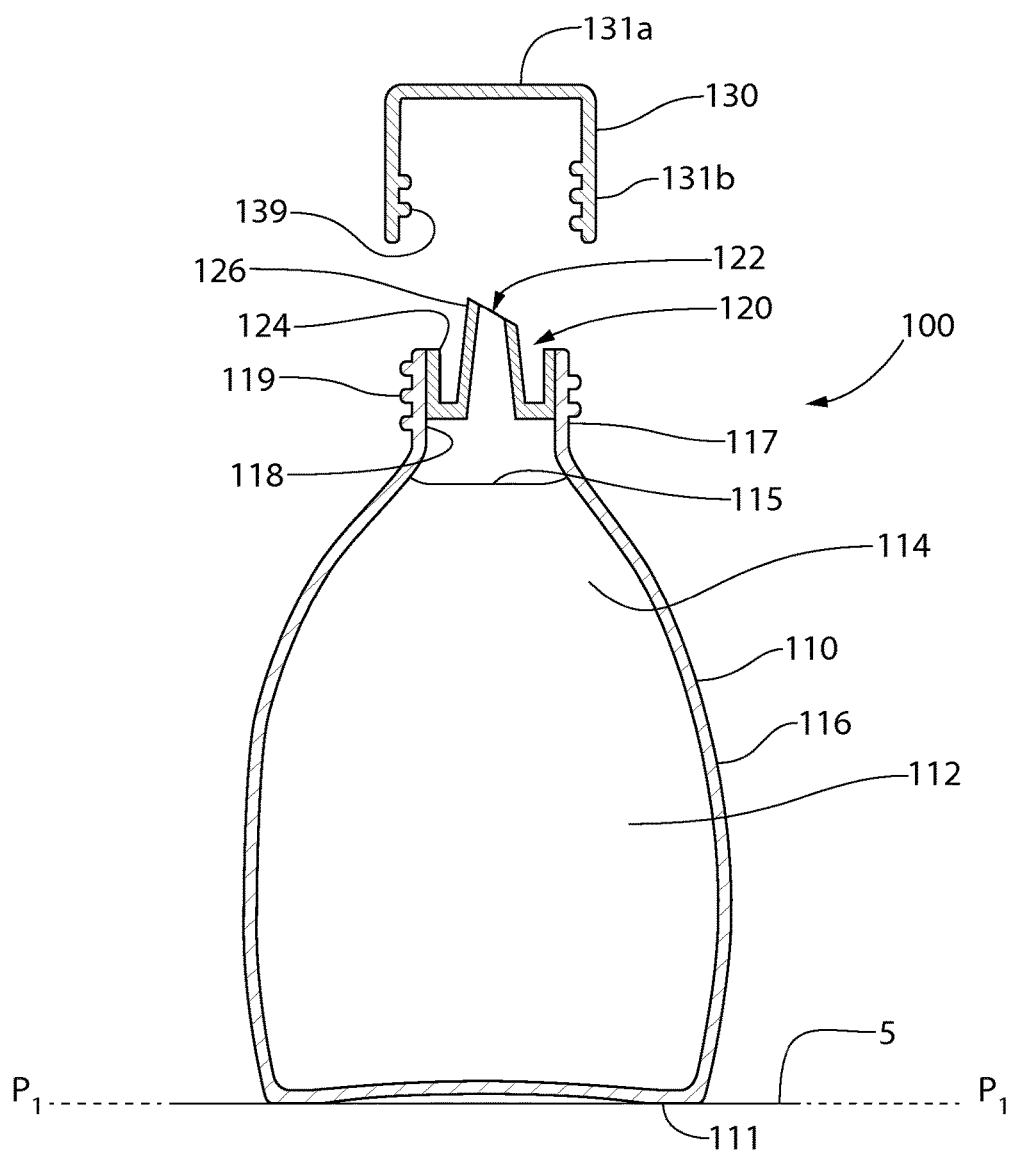
FIG. 1 shows a cross-sectional view of a container according to an embodiment of the present invention with a closure thereof at a second position relative to a vessel thereof.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

An embodiment of a container of the present invention will now be described with reference to FIG. 1. In short, the container 100 comprises a vessel 110 defining a chamber 112 storing a volume of a flowable substance 114 having a fragrance, a body 120 defining an opening 122 through which the flowable substance is dispensable from the chamber 112 and the container 100, and a closure 130 for selectively isolating the opening 122 from an exterior of the container 100. Each of the vessel 110, body 120 and closure 130 will be described in turn.

The vessel 110 includes a base 111 for supporting stably standing the container 100 on a horizontal support surface 5. In the illustrated embodiment, the base 111 comprises a planar, annular contact portion lying in a first plane $P_1$-$P_1$ for stably standing the vessel 110 and the rest of the container 100 on the horizontal support surface 5. In some variations to the illustrated embodiment, the base 111 comprises a planar, non-annular contact portion lying in the first plane $P_1$-$P_1$. For example, the base 111 may comprise a circular, elliptical, or polygonal contact portion. In some variations to the illustrated embodiment, the base 111 comprises a plurality of contact portions lying in the first plane $P_1$-$P_1$. In some variations to the illustrated embodiment, the base 111 comprises one or more non-planar contact portions lying in the first plane $P_1$-$P_1$, such as one or more point apexes or line apexes that are each a portion of a curved or non-planar surface of the vessel 110, yet the combination of the contact portion(s) of the base 111 enables the container 100 to stand stably on the horizontal support surface 5. Other configurations of contact portion(s) of the base 111 will be apparent to the skilled person.

As mentioned above, the vessel 110 defines the chamber 112 storing the volume of the flowable substance 114. Herein, by "flowable substance" it is meant a substance that is able to flow at room temperature and atmospheric pressure. Herein, by "room temperature" it is meant a temperature of 20 degrees Celsius, and by "atmospheric pressure" it is meant a pressure of 101 kPa. The flowable substance preferably is a liquid, although it could instead be any one of a paste, a powder, a gel, a foam, an emulsion and a sol. The flowable substance 114 may have the fragrance as a result of the flowable substance 114 comprising a fragrant agent. During manufacture of the flowable substance 114, the fragrant agent may be included in the flowable substance 114 to give the flowable substance 114 the fragrance. Alternatively or additionally, the flowable substance 114 may have the fragrance as a result of the flowable substance 114 comprising a flavoring agent, which flavoring agent has a fragrance. During manufacture of the flowable substance 114, the flavoring agent may be included in the flowable substance 114 primarily to give the flowable substance 114 a flavor, yet a secondary effect of the provision of the flavoring agent is to give the flowable substance 114 the fragrance. For example, in some embodiments, e.g. in some cases in which the flowable substance 114 is a mouthwash or other oral care substance, the flowable substance 114 may comprise a flavoring agent such as menthol or cinnamon, which primarily gives the flowable substance 114 a menthol or cinnamon flavor or taste but also gives the flowable substance 114 a menthol or cinnamon fragrance or smell. However the flowable substance 114 is manufactured, when provided in the chamber 112, the flowable substance 114 has a fragrance or smell detectable by the human nose.

In the illustrated embodiment, the vessel 110 is opaque. In variations to this embodiment, the vessel 110 may be partially, or fully, translucent or transparent, to allow a user to see how much flowable substance 114 remains in the chamber 112.

Whereas the chamber 112 is defined by a first portion 116 of the vessel 110, a second portion 117 of the vessel 110 is a neck 117 surrounding and defining an orifice 118, which orifice 118 has a smaller cross-sectional area parallel to the first plane $P_1$-$P_1$ than the chamber 112. The orifice 118 is at an interior of the neck 117 and is in fluid communication with the chamber 112. The vessel 110 is made from non-porous material, which in the illustrated embodiment is polypropylene (PP) but in other embodiments may be polyethylene terephthalate (PET) or another non-porous material, so that the only path from the chamber 112 to an exterior of the vessel 110 and the container 100 is via the orifice 118. An exterior surface of the neck 117 comprises a male screw thread 119 for connecting the closure 130 to the vessel 110, as will be described below.

The body 120, and more specifically a first portion 124 of the body 120, is affixed to the vessel 110. The first portion 124 of the body 120 is located in the orifice 118 defined by the neck 117 of the vessel 110 and is affixed to the neck 117 of the vessel 110. In the illustrated embodiment, the first portion 124 of the body 120 is affixed to the neck 117 of the vessel 110 by an adhesive. In variations to the illustrated embodiment, the first portion 124 of the body 120 may be affixed to the neck 117 of the vessel 110 in any other way, such as by any of a welded portion common to the body 120 and the vessel 110 (that is, the first portion 124 of the body 120 is welded to the neck 117 of the vessel 110), cooperating engagement members (such as screw threads) of the neck 117 and the first portion 124 of the body 120, a snap-fit connection, and an interference fit of the first portion 124 of the body 120 in the orifice 118. As in the illustrated embodiment, it is preferred that the body 120 is not detachable from the vessel 110, at least by an end user. However, in some embodiments, the body 120 may be detachably attached to the vessel 110.

A second portion 126 of the body 120 defines a spout 126 defining the opening 122 through which the flowable substance 114 is dispensable from the chamber 112 and the container 100. Accordingly, the opening 122 is fully defined by the body 120, so that the body 120 fully surrounds the opening 122, and the opening 122 is in fluid communication with the chamber 112 of the vessel 110. In the illustrated embodiment, the opening 122 is inclined relative to the first plane $P_1$-$P_1$. In variations to the illustrated embodiment, the opening 122 is parallel to the first plane $P_1$-$P_1$. In the illustrated embodiment, the second portion 126 of the body 120 is unitary with the first portion 124 of the body 120. That is, the body 120, comprising the first and second portions 124, 126, is an integrally-formed single component. In the illustrated embodiment, the body 120, i.e. the first and second portions 124, 126 of the body 120 together, is a porous element 120 that is suitable for retaining a quantity of the flowable substance 114. By "porous" it is meant having one or more pores, voids or interstices into, or through which, fluid, such as the flowable substance, is able to flow. In embodiments of the present invention, the porous element specifically is configured to be suitable for retaining the flowable substance in one or more of the pores, voids or interstices of the porous element. The body 120 is absorbent and, in the illustrated embodiment, is made from a sintered plastic. In variations to the illustrated embodiment, the body 120 may be made from wicking material, sintered plastic, pulp material, screen material, pressed paperboard, or another porous material. In a variation to the illustrated embodiment, the first portion 124 of the body 120 is not porous, whereas the second portion 126 of the body 120, which is unitary with the first portion 124 of the body 120, is a porous element that is suitable for retaining a quantity of the flowable substance 114.

The closure 130 is movable relative to the vessel 110 and the body 120 between a first position (not shown), at which the closure 130 isolates the opening 122, the chamber 112 and the volume of flowable substance 114 therein from the exterior of the container 100, and a second position (see FIG. 1), at which the opening 122, the chamber 112 and the volume of flowable substance 114 therein are in fluid communication with the exterior of the container 100. In the illustrated embodiment, when the closure 130 is at its first position relative to the vessel 110, the closure 130 does not block the opening 122 but still isolates the opening 122 from the exterior of the container 100. Specifically, the isolation is provided by a portion, such as a rim, of the closure 130 mating with the vessel 110 to create a seal therebetween. The isolation may, at least in part, be provided by the female screw thread 139 (discussed below) mating with the male screw thread 119. In a variation to the illustrated embodiment, the closure 130 does block the opening 122 when the closure 130 is at its first position relative to the vessel 110.

In the embodiment as shown, the closure 130 is a screw cap with a female screw thread 139 for mating with the male screw thread 119 at the exterior surface of the neck 117 of the vessel 110. The closure 130 is movable relative to the vessel 110 between the first and second positions by rotating the closure 130 relative to the vessel 110 to engage and disengage the screw threads 119, 139, as required. The closure 130 comprises a floor 131a and a skirt 131b extending from the floor 131a. The female screw thread 139 is provided on an interior face of the skirt 131b. In variations to the illustrated embodiment, the vessel 110, body 120 and closure 130 may be suitably modified from the embodiment of FIG. 1 so that the screw thread 139 of the closure 130 is male and the screw thread 119 of the vessel 110 is female and mateable with the screw thread 139 of the closure 130. Moreover, in other variations to the illustrated embodiment, the closure 130 may be detachably connectable to the vessel 110 using mechanisms other than cooperating screw threads. In such other variations to the illustrated embodiment, the screw threads 119, 139 may be omitted.

In the illustrated embodiment, when the closure 130 is at the first position (not shown) relative to the vessel 110, the body 120 is in fluid communication with the chamber 112 and the volume of flowable substance 114 therein, but the body 120 is isolated from the exterior of the container 100. On the other hand, when the closure 130 is at the second position relative to the vessel 110 (as shown), the body 120 is in fluid communication with the chamber 112 and the volume of flowable substance 114 therein, and with the exterior of the container 100. Also, when the closure 130 is at the second position relative to the vessel 110, the closure 130 is disconnected from the vessel 110. In variations to the illustrated embodiment, when the closure 130 is at the second position relative to the vessel 110, the closure 130 may remain connected to the vessel 110, for example by a hinge, such as a living hinge formed integrally with the closure 130 and the vessel 110.

When the container 100 is in a storage state with the closure 130 at its first position relative to the vessel 110 and with the base 111 of the vessel 110 in contact with the horizontal support surface 5 and the plane $P_1$-$P_1$ parallel to the horizontal support surface 5, although the body 120 is in fluid communication with the chamber 112 and the volume of the flowable substance 114 in the chamber 112, the body 120 is out of contact with the volume of the flowable substance 114 in the chamber 112. That is, an uppermost surface 115 of the flowable substance 114 in the chamber 112 is between the plane $P_1$-$P_1$ and the body 120 but out of contact with the body 120. However, when the container 100 is tilted sufficiently relative to the horizontal during transportation to a retailer, or when being put on a shelf in a retailer's shop or store, the flowable substance 114 comes into contact with the body 120. Since the body 120 is porous, when the flowable substance 114 comes into contact with the body 120, the body 120 retains a quantity of the flowable substance 114. Accordingly, when a potential purchaser subsequently moves the closure 130 to its second position relative to the vessel 110 and sniffs the opening 122 to determine the fragrance of the flowable substance 114, the fragrance is delivered not only through the opening 122 from the volume of the flowable substance 114 within the chamber 112 but also from the body 120 itself. That is, in contrast to a comparative example in which the body 120 is not porous and retains little or none of the flowable substance, in the container 100 of FIG. 1 a greater surface area is provided from which the fragrance is deliverable to a user. The porous element captures, or becomes infused with, the flowable substance 114 and its fragrance either by simple contact with the flowable substance 114 or by capillary action as a result of coming into contact with the flowable substance 114. A potential purchaser is thus able to determine accurately the fragrance of the flowable substance 114 prior to purchasing the container 100.

Improved delivery of the fragrance continues after a user has purchased the container 100. As will be appreciated from consideration of FIG. 1, the body 120 is at a position relative to the volume of the flowable substance 114 so that the flowable substance 114 comes into contact with the body 120 as a result of the flowable substance 114 being dispensed from the chamber 112 through the opening 122. More specifically, the body 120 is at a position relative to the volume of the flowable substance 114 so that the flowable substance 114 comes into contact with the body 120 as the flowable substance 114 is dispensed from the chamber 112 through the opening 122. That is, the body 120 is on a flow path extending between the chamber 112 and the opening 122. Every time the user tilts the container 100 sufficiently relative to the horizontal to dispense the flowable substance 114 from the chamber 112 through the opening 122, the flowable substance 114 comes into contact with the body 120, and the body 120 retains a quantity of the flowable substance 114. Therefore, even if, over time, some of the flowable substance 114 retained by the body 120 moves from the body 120 to the chamber 112 under the influence of gravity, at every dispensing operation the body 120 is recharged with a quantity of the flowable substance 114. Accordingly, throughout the working lifetime of the container 100, i.e. while some of the flowable substance 114 remains in the container 100 and a user repeatedly dispenses some of the flowable substance 114, the user is able to sniff the opening 122 to determine accurately the fragrance of the flowable substance 114.

Another embodiment of a container of the present invention will now be described with reference to FIG. 2. Like elements in FIGS. 1 and 2 have like reference numerals and will not be described again for conciseness. Any of the above-described possible variations to the preceding described container may be made to the container of FIG. 2.

Figure 2:
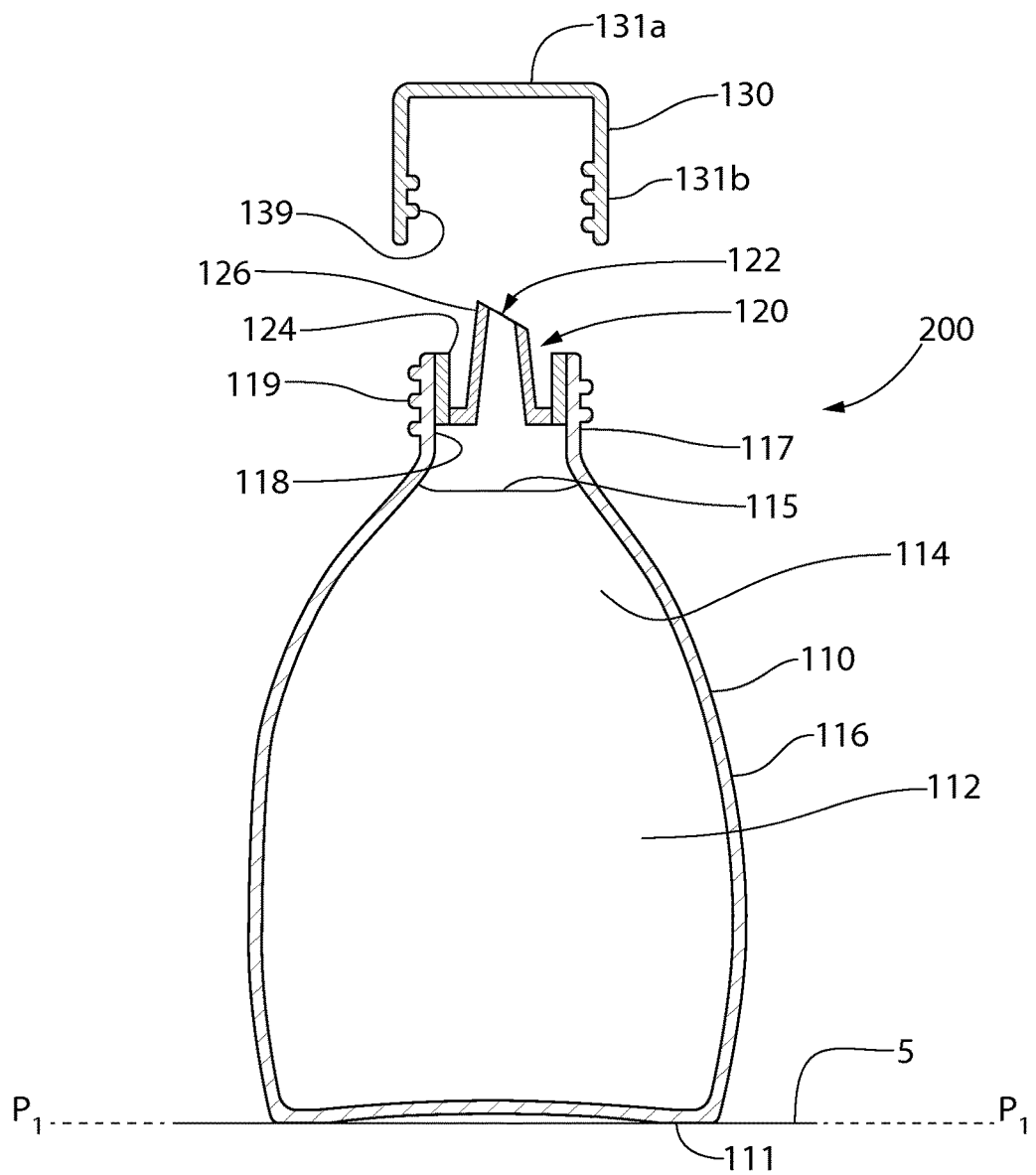
FIG. 2 shows a cross-sectional view of a container according to another embodiment of the present invention with a closure thereof at a second position relative to a vessel thereof.

The container 200 of FIG. 2 differs from the container 100 of FIG. 1 only in the form of the body 120. In the container 200 of FIG. 2, the second portion 126 of the body 120, which second portion 126 defines the spout, is not unitary with the first portion 124 of the body 120. Instead, the second portion 126 of the body 120 is affixed to the first portion 124 of the body 120 by an adhesive. In variations to the illustrated embodiment, the second portion 126 of the body 120 may be affixed to the first portion 124 of the body 120 in any other way, such as by any of a welded portion common to the first and second portions 124, 126 of the body 120, cooperating engagement members (such as screw threads) first and second portions 124, 126 of the body 120, a snap-fit connection, and an interference fit of the second portion 126 of the body 120 in the first portion 124 of the body 120.

In the container 200 of FIG. 2, the first portion 124 of the body 120 is a non-porous member, whereas the second portion 126 of the body 120 is a porous element that is suitable for retaining a quantity of the flowable substance 114. The opening 122 is fully defined by the second portion 126 of the body 120, and the second portion 126 of the body 120 fully surrounds the opening 122. In a variation to the illustrated embodiment, the second portion 126 of the body 120 is a non-porous member, whereas the first portion 124 of the body 120 is porous and is an element that is suitable for retaining a quantity of the flowable substance 114. In such a variation to the illustrated embodiment, the opening 122 is fully defined by the second portion 126 of the body 120, i.e. by the member, yet the first portion 124 of the body 120 fully surrounds the opening 122. In a still further variation to the illustrated embodiment, each of the first and second portions 124, 126 of the body 120 is porous and is an element that is suitable for retaining a quantity of the flowable substance 114.

The container 200 of FIG. 2 is operable in a similar manner to container 100 of FIG. 1. When the container 200 is in a storage state with the closure 130 at its first position relative to the vessel 110, the second portion 126 of the body 120 is in fluid communication with the chamber 112 and the volume of the flowable substance 114 in the chamber 112, yet the second portion 126 of the body 120 is out of contact with the volume of the flowable substance 114 in the chamber 112. When the container 200 is tilted sufficiently relative to the horizontal during transportation to a retailer, or when being put on a shelf in a retailer's shop or store, the flowable substance 114 comes into contact with the second portion 126 of the body 120 and the second portion 126 of the body 120 retains a quantity of the flowable substance 114. Moreover, every time the user tilts the container 200 sufficiently relative to the horizontal to dispense the flowable substance 114 from the chamber 112 through the opening 122, the flowable substance 114 comes into contact with the second portion 126 of the body 120, and the second portion 126 of the body 120 retains a quantity of the flowable substance 114. Accordingly, prior to, and after, purchase of the container 200, a fragrance of the flowable substance 114 is delivered not only through the opening 122 from the volume of the flowable substance 114 within the chamber 112 but also from the second portion 126 of the body 120. Thus, a potential purchaser or a user is able to sniff the opening 122 to determine accurately the fragrance of the flowable substance 114.

Another embodiment of a container of the present invention will now be described with reference to FIG. 3. Like elements in FIGS. 1 and 3 have like reference numerals and will not be described again for conciseness. Any of the above-described possible variations to the preceding described containers may be made to the container of FIG. 3.

Figure 3:
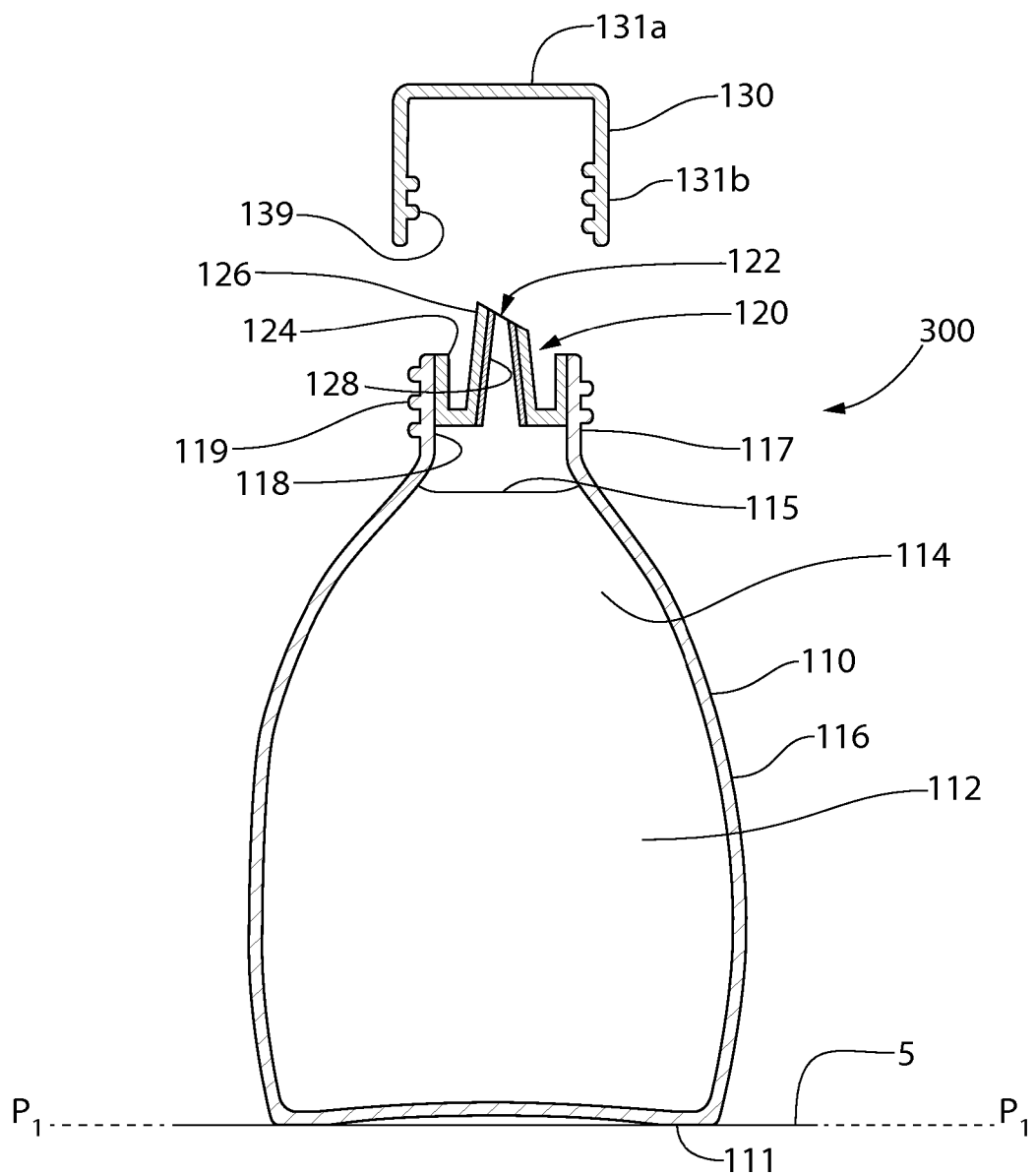
FIG. 3 shows a cross-sectional view of a container according to another embodiment of the present invention with a closure thereof at a second position relative to a vessel thereof.

The container 300 of FIG. 3 differs from the container 100 of FIG. 1 only in the form of the body 120. In the container 300 of FIG. 3, the first and second portions 124, 126 of the body 120 are unitary and together form a non-porous member, and the body 120 comprises a third portion 128. The third portion 128 of the body 120 is an annular porous element that is suitable for retaining a quantity of the flowable substance 114. The opening 122 is fully defined by the third portion 128 of the body 120, each of the second and third portions 126, 128 of the body 120 fully surround the opening 122, and the second and third portions 126, 128 of the body 120 together define the spout. The third portion 128 of the body 120 is a liner affixed to a radially inner surface of the second portion 126 of the body 120, i.e. to the member, preferably by an adhesive. In a variation to the illustrated embodiment, the third portion 128 of the body 120 is not annular and only partially surrounds the opening 122. In such a variation, the opening 122 is partially defined by the member and partially defined by the third portion 128 of the body 120. In some variations to the illustrated embodiment, the third portion 128 of the body 120 is not a liner but nevertheless still is affixed to the radially inner surface of the member.

The container 300 of FIG. 3 is operable in a similar manner to container 100 of FIG. 1. When the container 300 is in a storage state with the closure 130 at its first position relative to the vessel 110, the third portion 128 of the body 120 is in fluid communication with the chamber 112 and the volume of the flowable substance 114 in the chamber 112, yet the third portion 128 of the body 120 is out of contact with the volume of the flowable substance 114 in the chamber 112. When the container 300 is tilted sufficiently relative to the horizontal during transportation to a retailer, or when being put on a shelf in a retailer's shop or store, the flowable substance 114 comes into contact with the third portion 128 of the body 120 and the third portion 128 of the body 120 retains a quantity of the flowable substance 114. Moreover, every time the user tilts the container 300 sufficiently relative to the horizontal to dispense the flowable substance 114 from the chamber 112 through the opening 122, the flowable substance 114 comes into contact with the third portion 128 of the body 120, and the third portion 128 of the body 120 retains a quantity of the flowable substance 114. Accordingly, prior to, and after, purchase of the container 300, a fragrance of the flowable substance 114 is delivered not only through the opening 122 from the volume of the flowable substance 114 within the chamber 112 but also from the third portion 128 of the body 120. Thus, a potential purchaser or a user is able to sniff the opening 122 to determine accurately the fragrance of the flowable substance 114.

Another embodiment of a container of the present invention will now be described with reference to FIGS. 4a and 4b. Like elements in FIGS. 3, 4a and 4b have like reference numerals and will not be described again for conciseness. Any of the above-described possible variations to the preceding described containers may be made to the container of FIGS. 4a and 4b.

Figure 4A:
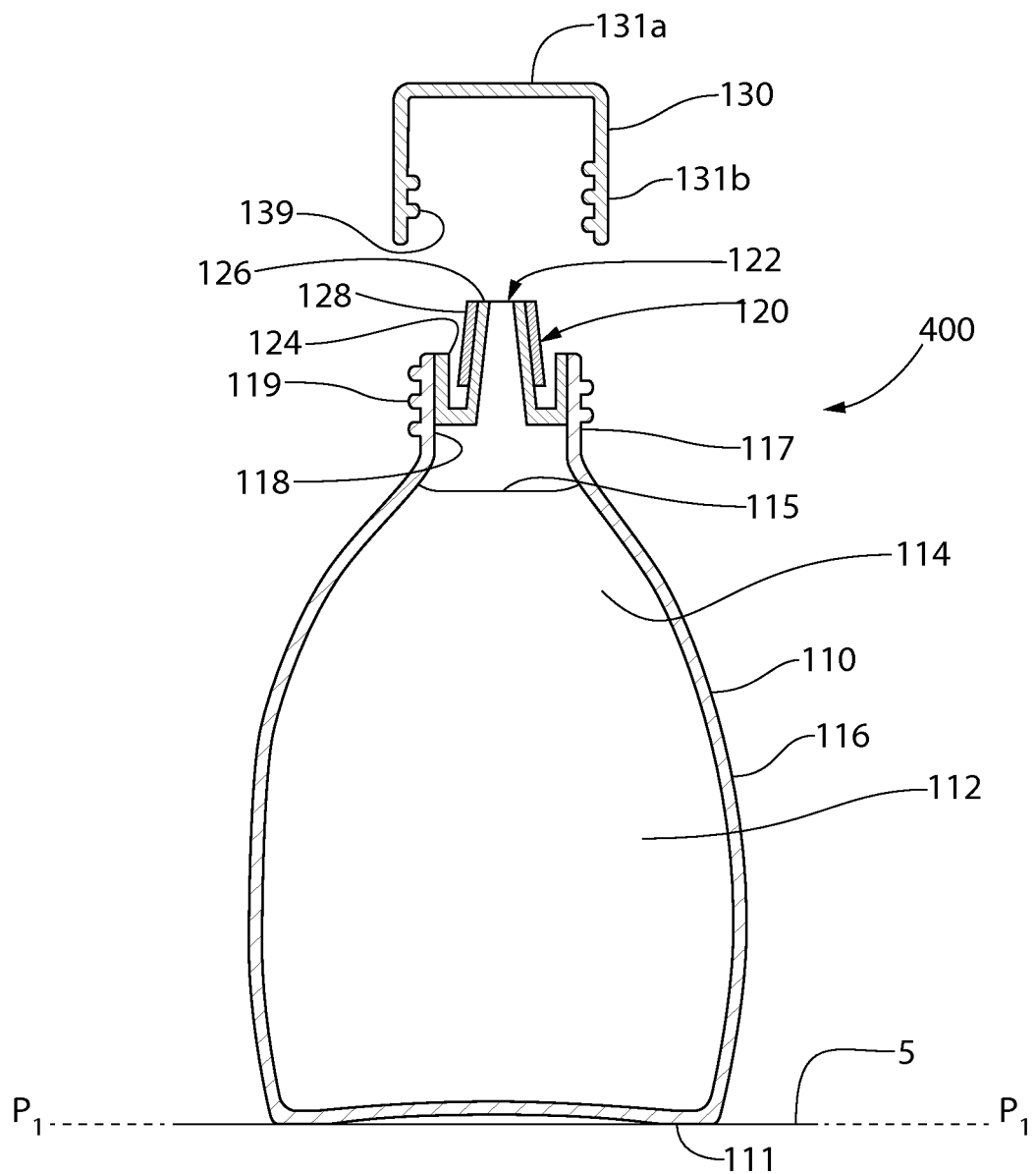
FIG. 4a shows a cross-sectional view of a container according to a further embodiment of the present invention with a closure thereof at a second position relative to a vessel thereof.
Figure 4B:
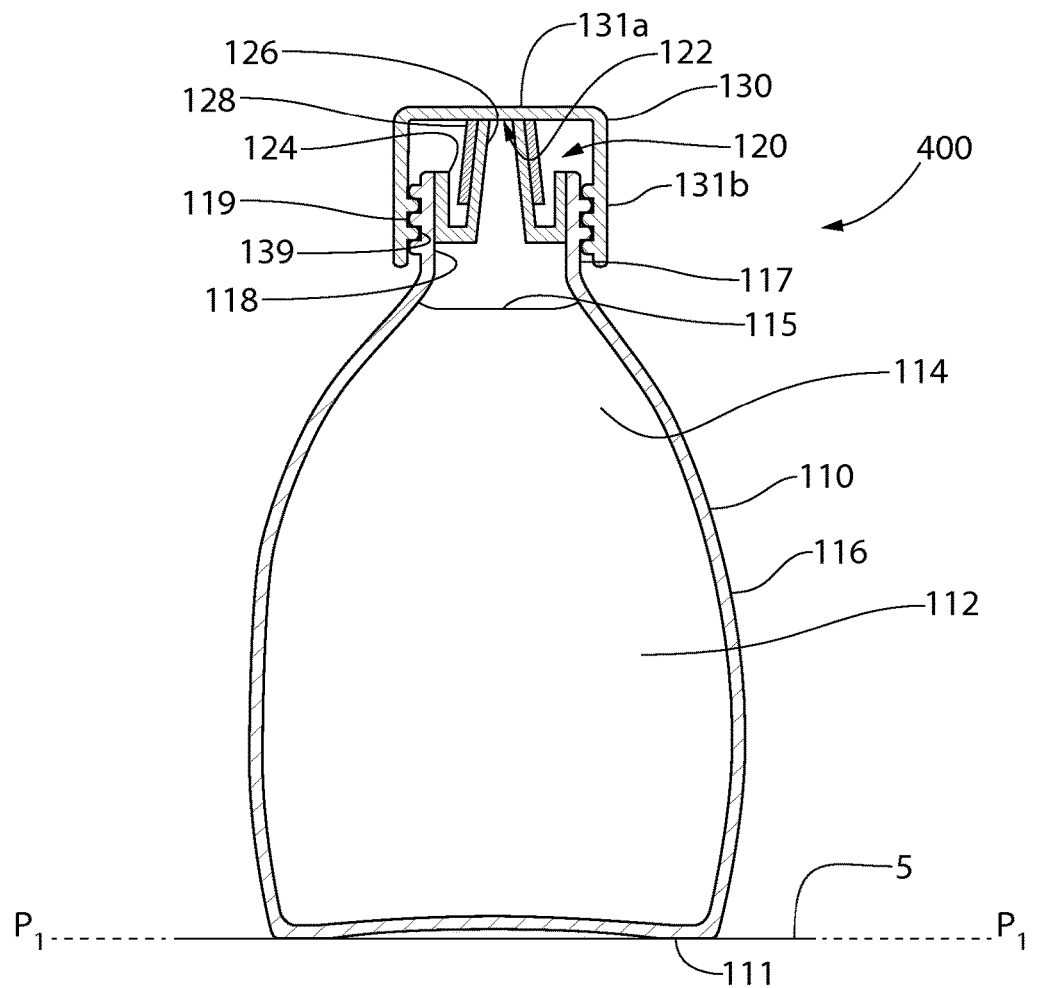
FIG. 4b shows a cross-sectional view of the container of FIG. 4a with the closure thereof at a first position relative to the vessel.

The container 400 of FIGS. 4a and 4b differs from the container 300 of FIG. 3 only in the form of the body 120. In the container 400 of FIGS. 4a and 4b, the first and second portions 124, 126 of the body 120 are unitary and together form a non-porous member, and the third portion 128 of the body 120 is a liner affixed to a radially outer surface of the second portion 126 of the body 120, i.e. to the member, preferably by an adhesive. The third portion 128 of the body 120 still is an annular porous element that is suitable for retaining a quantity of the flowable substance 114. The opening 122 is fully defined by the second portion 126 of the body 120, each of the second and third portions 126, 128 of the body 120 fully surround the opening 122, and the second and third portions 126, 128 of the body 120 together define the spout. In a variation to the illustrated embodiment, the third portion 128 of the body 120 is not annular and only partially surrounds the opening 122. In some variations to the illustrated embodiment, the third portion 128 of the body 120 is not a liner but nevertheless still is affixed to the radially outer surface of the member.

In contrast to the containers 100, 200, 300 of FIGS. 1 to 3, when the closure 130 of the container 400 of FIGS. 4a and 4b is at the first position relative to the vessel 110 (see FIG. 4b), the porous element, i.e. the third portion 128 of the body 120, is isolated from the chamber 112 and the volume of flowable substance 114 therein, and also from the exterior of the container 400, by the closure 130. On the other hand, when the closure 130 is at the second position relative to the vessel 110 (see FIG. 4a), the third portion 128 of the body 120 is in fluid communication with the chamber 112 and the volume of flowable substance 114 therein, and also with the exterior of the container 400. In a variation to the illustrated embodiment, the body 120 and closure 130 are relatively shaped so that, when the closure 130 is at the first position relative to the vessel 110, the porous element, i.e. the third portion 128 of the body 120, is in fluid communication with the chamber 112 and the volume of flowable substance 114 therein.

The container 400 of FIGS. 4a and 4b is operable in a slightly different manner to containers 100, 200, 300 of FIGS. 1 to 3. When the container 400 of FIGS. 4a and 4b is in a storage state and the closure 130 is at its first position relative to the vessel 110 (see FIG. 4b), even if the container 400 is tilted 180 degrees (i.e. is turned upside down) relative to the horizontal during transportation to a retailer, or when being put on a shelf in a retailer's shop or store, the closure 130 prevents the flowable substance 114 from coming into contact with the third portion 128 of the body 120. However, when the closure 130 is at its second position relative to the vessel 110, after a user has tilted the container 400 sufficiently relative to the horizontal to dispense the flowable substance 114 from the chamber 112 through the opening 122 and has subsequently returned the container 400 back towards its original position relative to the horizontal, some of the flowable substance 114 remaining at the opening 122 will run down the radial outside surface of the body 120, i.e. will come into contact with the third portion 128 of the body 120. Thus, the third portion 128 of the body 120 would retain a quantity of the flowable substance 114. Accordingly, after some of the flowable substance 114 has been dispensed, a fragrance of the flowable substance 114 is delivered not only through the opening 122 from the volume of the flowable substance 114 within the chamber 112 but also from the third portion 128 of the body 120. Thus, a user is able to sniff around the opening 122 to determine accurately the fragrance of the flowable substance 114.

It will be appreciated that, in the container 400 of FIGS. 4a and 4b, the third portion 128 of the body 120 is not at a position relative to the volume of the flowable substance 114 so that the flowable substance 114 comes into contact with the third portion 128 of the body 120 as the flowable substance 114 is dispensed from the chamber 112 through the opening 122. That is, the third portion 128 of the body 120 is not on a flow path extending between the chamber 112 and the opening 122. However, the third portion 128 of the body 120 is at a position relative to the volume of the flowable substance 114 so that the flowable substance 114 comes into contact with the third portion 128 of the body 120 as a result of the flowable substance 114 being dispensed from the chamber 112 through the opening 122.

Figure 5A:
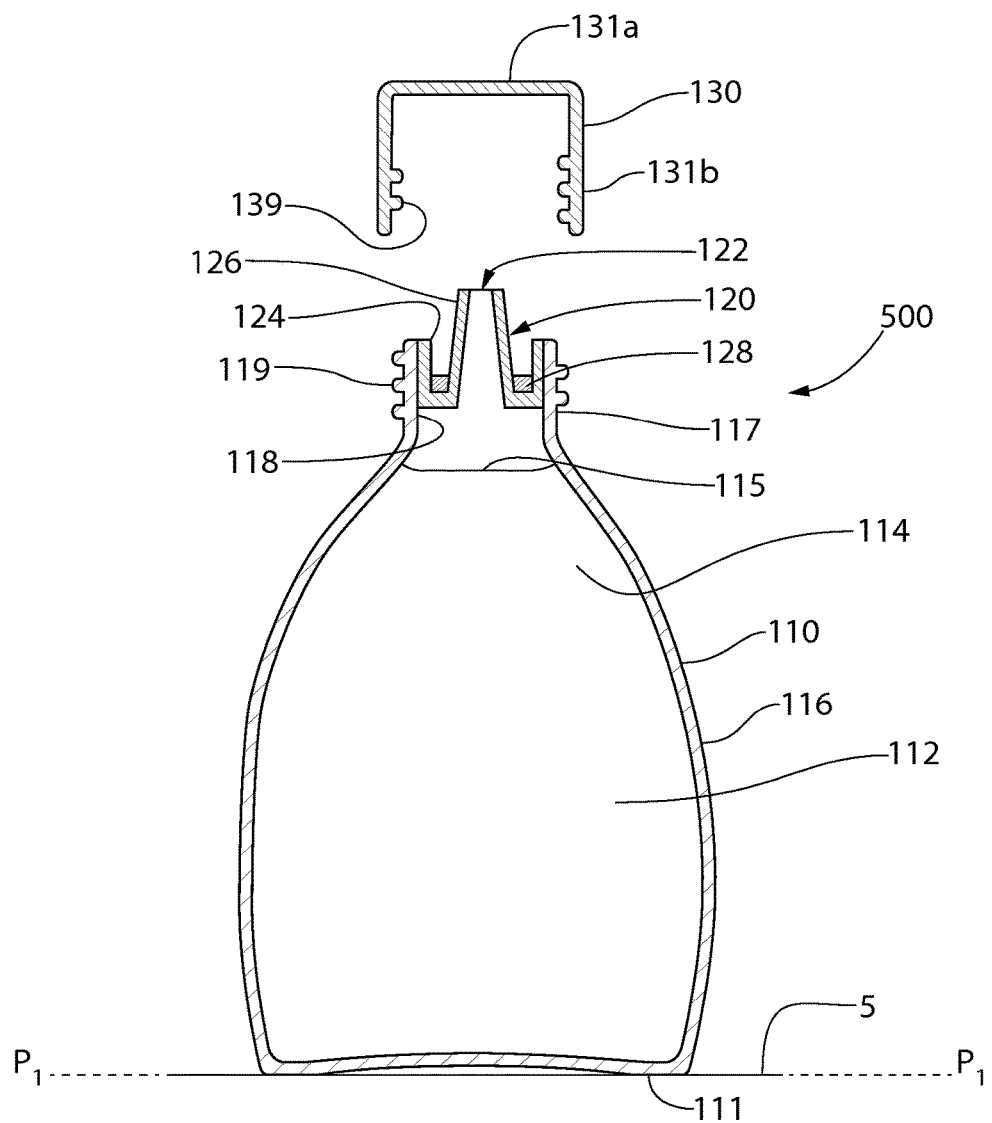
FIG. 5a shows a cross-sectional view of a container according to a further embodiment of the present invention with a closure thereof at a second position relative to a vessel thereof.
Figure 5B:
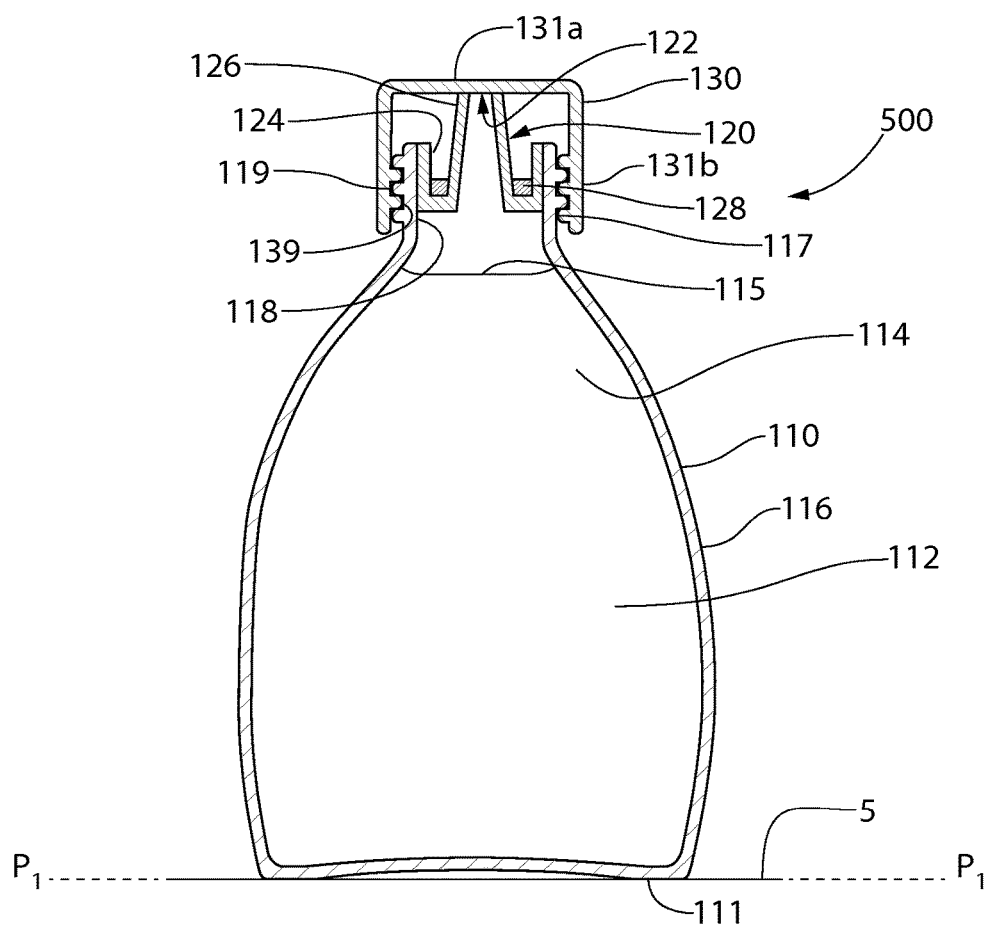
FIG. 5b shows a cross-sectional view of the container of FIG. 5a with the closure thereof at a first position relative to the vessel.

Another embodiment of a container of the present invention is shown in FIGS. 5a and 5b. Like elements in FIGS. 4a, 4b, 5a and 5b have like reference numerals and will not be described again for conciseness. Any of the above-described possible variations to the preceding described containers may be made to the container of FIGS. 5a and 5b.

The container 500 of FIGS. 5a and 5b differs from the container 400 of FIGS. 4a and 4b only in the form of the third portion 128 of the body 120. In the container 500 of FIGS. 5a and 5b, the third portion 128 of the body 120 is affixed to both the first and second portions 124, 126 of the body 120, i.e. to the member, preferably by an adhesive. The third portion 128 of the body 120 still is an annular porous element that is suitable for retaining a quantity of the flowable substance 114. The opening 122 is fully defined by the second portion 126 of the body 120, the second portion 126 of the body 120 fully surrounds the opening 122, and the second portion 126 of the body 120 defines the spout. In a variation to the illustrated embodiment, the third portion 128 of the body 120 is not annular.

As for the container 400 of FIGS. 4a and 4b, when the closure 130 of the container 500 of FIGS. 5a and 5b is at the first position relative to the vessel 110 (see FIG. 5b), the porous element, i.e. the third portion 128 of the body 120, is isolated from the chamber 112 and the volume of flowable substance 114 therein by the closure 130, and also is isolated from the exterior of the container 500 by the closure 130. On the other hand, when the closure 130 is at the second position relative to the vessel 110 (see FIG. 5a), the third portion 128 of the body 120 is in fluid communication with the chamber 112 and the volume of flowable substance 114 therein, and also with the exterior of the container 500. In a variation to the illustrated embodiment, the body 120 and closure 130 are relatively shaped so that, when the closure 130 is at the first position relative to the vessel 110, the porous element, i.e. the third portion 128 of the body 120, is in fluid communication with the chamber 112 and the volume of flowable substance 114 therein.

The container 500 of FIGS. 5a and 5b is operable in the same manner as the container 400 of FIGS. 4a and 4b. Accordingly, it will be appreciated that, in the container 500 of FIGS. 5a and 5b, the third portion 128 of the body 120 is not at a position relative to the volume of the flowable substance 114 so that the flowable substance 114 comes into contact with the third portion 128 of the body 120 as the flowable substance 114 is dispensed from the chamber 112 through the opening 122. However, the third portion 128 of the body 120 is at a position relative to the volume of the flowable substance 114 so that the flowable substance 114 comes into contact with the third portion 128 of the body 120 as a result of the flowable substance 114 being dispensed from the chamber 112 through the opening 122.

Figure 6A:
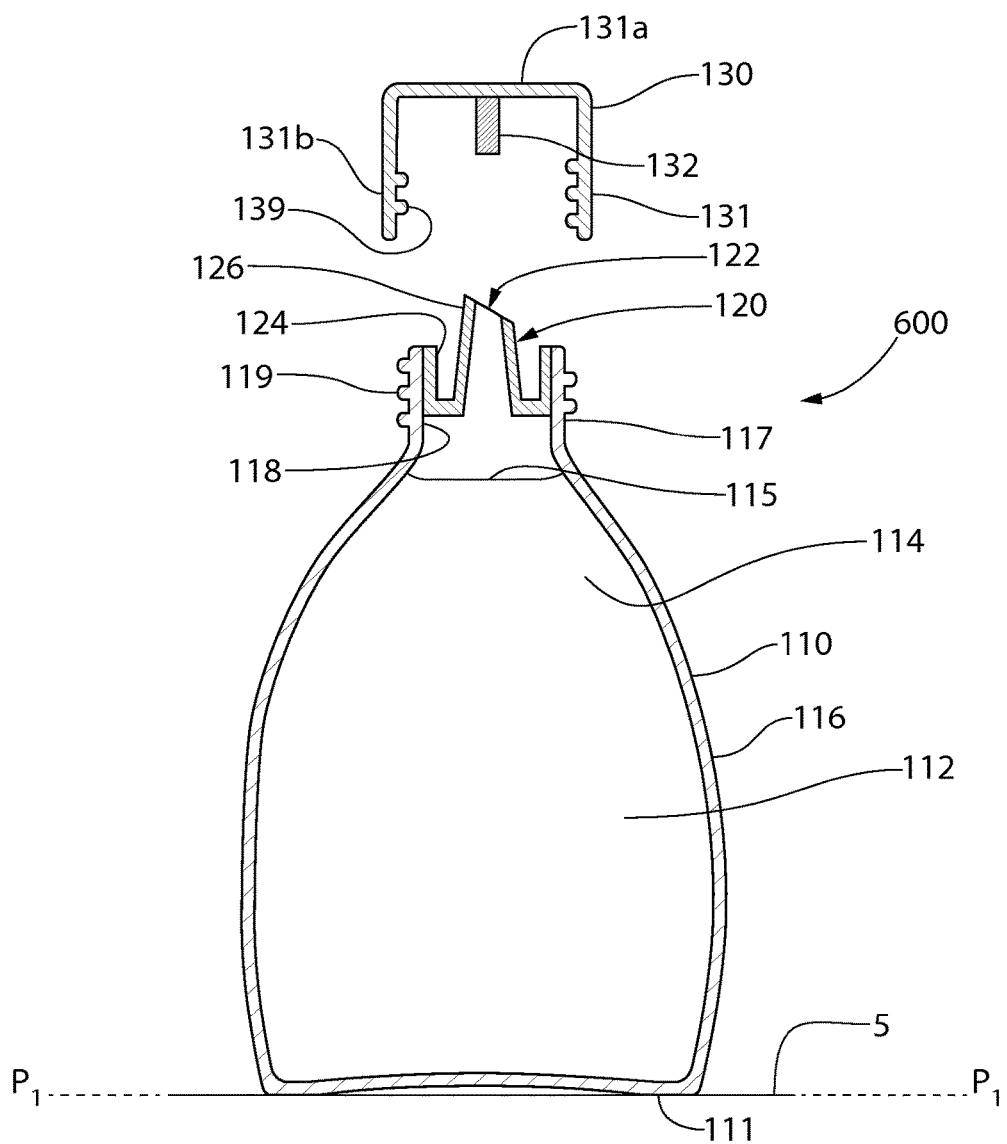
FIG. 6a shows a cross-sectional view of a container according to a further embodiment of the present invention with a closure thereof at a second position relative to a vessel thereof.
Figure 6B:
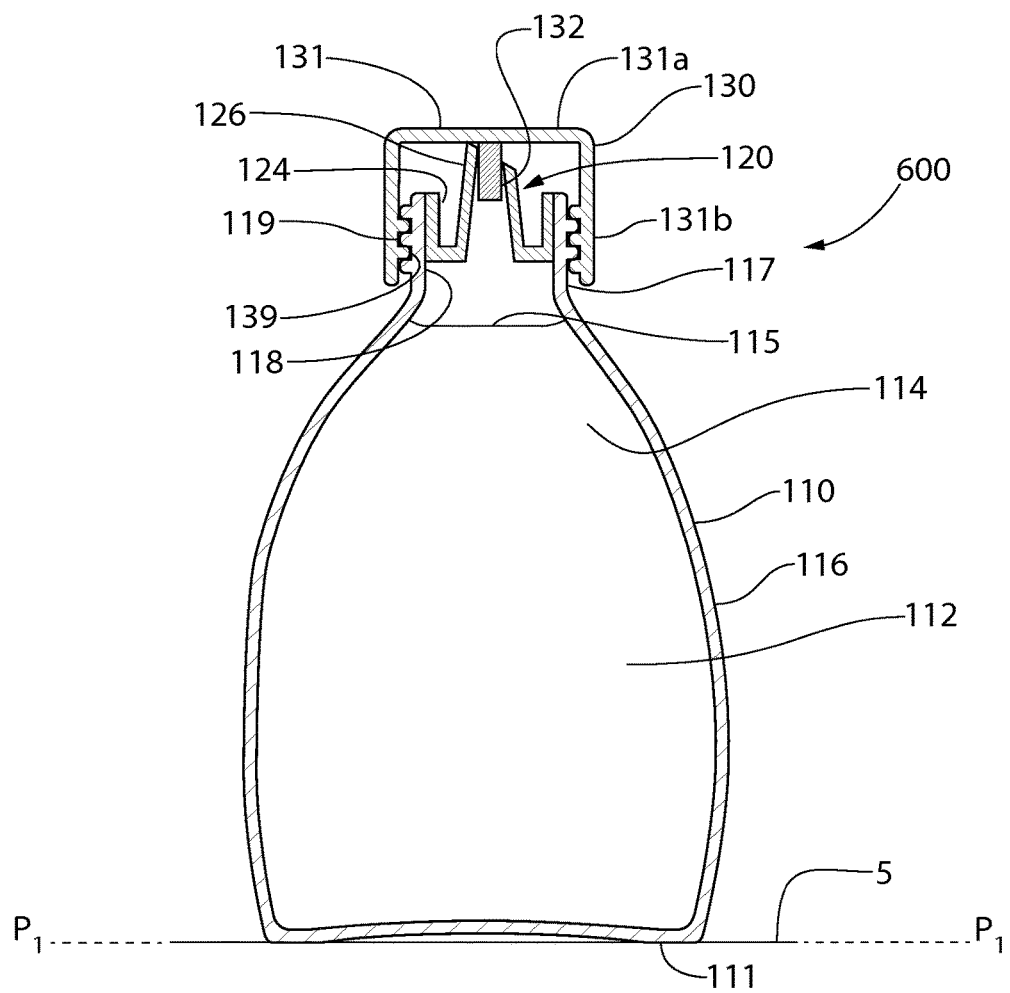
FIG. 6b shows a cross-sectional view of the container of FIG. 6a with the closure thereof at a first position relative to the vessel.

Another embodiment of a container of the present invention is shown in FIGS. 6a and 6b. Like elements in FIGS. 5a, 5b, 6a and 6b have like reference numerals and will not be described again for conciseness. Any of the above-described possible variations to the preceding described containers may be made to the container of FIGS. 6a and 6b.

The container 600 of FIGS. 6a and 6b differs from the container 500 of FIGS. 5a and 5b only in the location of the porous element for retaining a quantity of the flowable substance 114. In contrast to the containers 100, 200, 300, 400, 500 of FIGS. 1 to 5b, in the container 600 of FIGS. 6a and 6b the porous element for retaining a quantity of the flowable substance 114 is comprised in the closure 130 rather than in the body 120.

More specifically, the body 120, comprising the first and second portions 124, 126, which are unitary, is a non-porous member. The opening 122 is fully defined by the second portion 126 of the body 120, the second portion 126 of the body 120 fully surrounds the opening 122, and the second portion 126 of the body 120 defines the spout. The body 120 is free of any porous element for retaining a quantity of the flowable substance 114. However, in respective variations to the embodiment of FIGS. 6a and 6b, the container 600 may comprise any of the porous elements discussed above and shown in FIGS. 1 to 6b in the body 120, as well as the porous element 132 comprised in the closure 130.

The closure 130 comprises a closure member 131, in the form of a screw cap, and the porous element 132 is affixed to the closure member 131, preferably by adhesive. In a variation to this embodiment, the porous element 132 is unitary with the closure member 131. The closure member 131 comprises a floor 131a and a skirt 131b depending from the floor 131a. The female screw thread 139 is provided on an interior face of the skirt 131b. The porous element 132 is an elongate element affixed to the floor 131a of the closure member 131 so that the porous element 132 is elongate in a direction extending from the floor 131a and the skirt 131b surrounds the porous element 132. The skirt 131b and the porous element 132 are spaced apart. The porous element 132 is dimensioned so as to be able to fit in the opening 122 defined by the body 120.

The closure 130 is movable relative to the vessel 110 between a first position (see FIG. 6b) at which a portion of the porous element 132 of the closure 130 is in the opening 122 and the closure 130 blocks the opening 122, and a second position (see FIG. 6a) at which none of the porous element 132 is in the opening 122 and the opening 122 is not blocked by the closure 130. In the illustrated embodiment, when the closure 130 is at the first position relative to the vessel 110, the porous element 132 blocks the opening 122. In a variation to the illustrated embodiment, when the closure 130 is at the first position relative to the vessel 110, at least a portion of the porous element 132 is in the opening 122 but the closure 130, including the porous element 132, does not block the opening 122. In any case, when the closure 130 is at the first position relative to the vessel 110, the porous element 132 is in fluid communication with the chamber 112 and the volume of flowable substance 114 therein, but the porous element 132 is isolated from the exterior of the container 600. On the other hand, when the closure 130 is at the second position relative to the vessel 110, the porous element 132 is in fluid communication with the chamber 112 and the volume of flowable substance 114 therein, and with the exterior of the container 600.

In FIG. 6b the container 600 is shown in a storage state with the base 111 of the vessel 110 in contact with the horizontal support surface 5 and the plane $P_1$-$P_1$ parallel to the horizontal support surface 5. In this storage state, although the porous element 132 is in fluid communication with the chamber 112 and the volume of the flowable substance 114 in the chamber 112, the porous element 132 is out of contact with the volume of the flowable substance 114 in the chamber 112. That is, an uppermost surface 115 of the flowable substance 114 in the chamber 112 is between the plane $P_1$-$P_1$ and the porous element 132 but out of contact with the porous element 132. However, when the container 600 is tilted sufficiently relative to the horizontal during transportation to a retailer, or when being put on a shelf in a retailer's shop or store, the flowable substance 114 comes into contact with the porous element 132, and the porous element 132 retains a quantity of the flowable substance 114. Accordingly, when a potential purchaser subsequently moves the closure 130 to its second position relative to the vessel 110 and sniffs to determine the fragrance of the flowable substance 114, the fragrance is delivered not only through the opening 122 from the volume of the flowable substance 114 within the chamber 112 but also from the porous element 132 of the closure 130. A potential purchaser is thus able to determine accurately the fragrance of the flowable substance 114 prior to purchase of the container 600.

Improved delivery of the fragrance continues after a user has purchased the container 600. For example, when the container 600 is tilted sufficiently relative to the horizontal during transportation around the user's residence, the flowable substance 114 comes into contact with the porous element 132, and the porous element 132 retains a quantity of the flowable substance 114. Moreover, when the closure 130 is at its second position relative to the vessel 110, after a user has tilted the container 600 sufficiently relative to the horizontal to dispense the flowable substance 114 from the chamber 112 through the opening 122 and has subsequently returned the container 600 back towards its original position relative to the horizontal, a residual volume of the flowable substance 114 will remain on a surface of the second portion 126 of the body 120 at the opening 122. When the user subsequently returns the closure 130 to its first position relative to the vessel 110, the porous element 132 would come into contact with the residual volume of the flowable substance 114, and the porous element 132 would retain a quantity of the flowable substance 114. Therefore, at least at every dispensing operation, the porous element 132 is recharged with a quantity of the flowable substance 114. Accordingly, throughout the working lifetime of the container 600, i.e. while some of the flowable substance 114 remains in the container 600 and a user repeatedly dispenses some of the flowable substance 114, the user is able to sniff the closure 130 to determine accurately the fragrance of the flowable substance 114.

It will be appreciated that, in the container 600 of FIGS. 6a and 6b, the porous element 132 is not at a position relative to the volume of the flowable substance 114 so that the flowable substance 114 comes into contact with the porous element 132 as the flowable substance 114 is dispensed from the chamber 112 through the opening 122. However, the porous element 132 is at a position relative to the volume of the flowable substance 114 so that the flowable substance 114 comes into contact with porous element 132 as a result of the flowable substance 114 being dispensed from the chamber 112 through the opening 122.

Figure 7A:
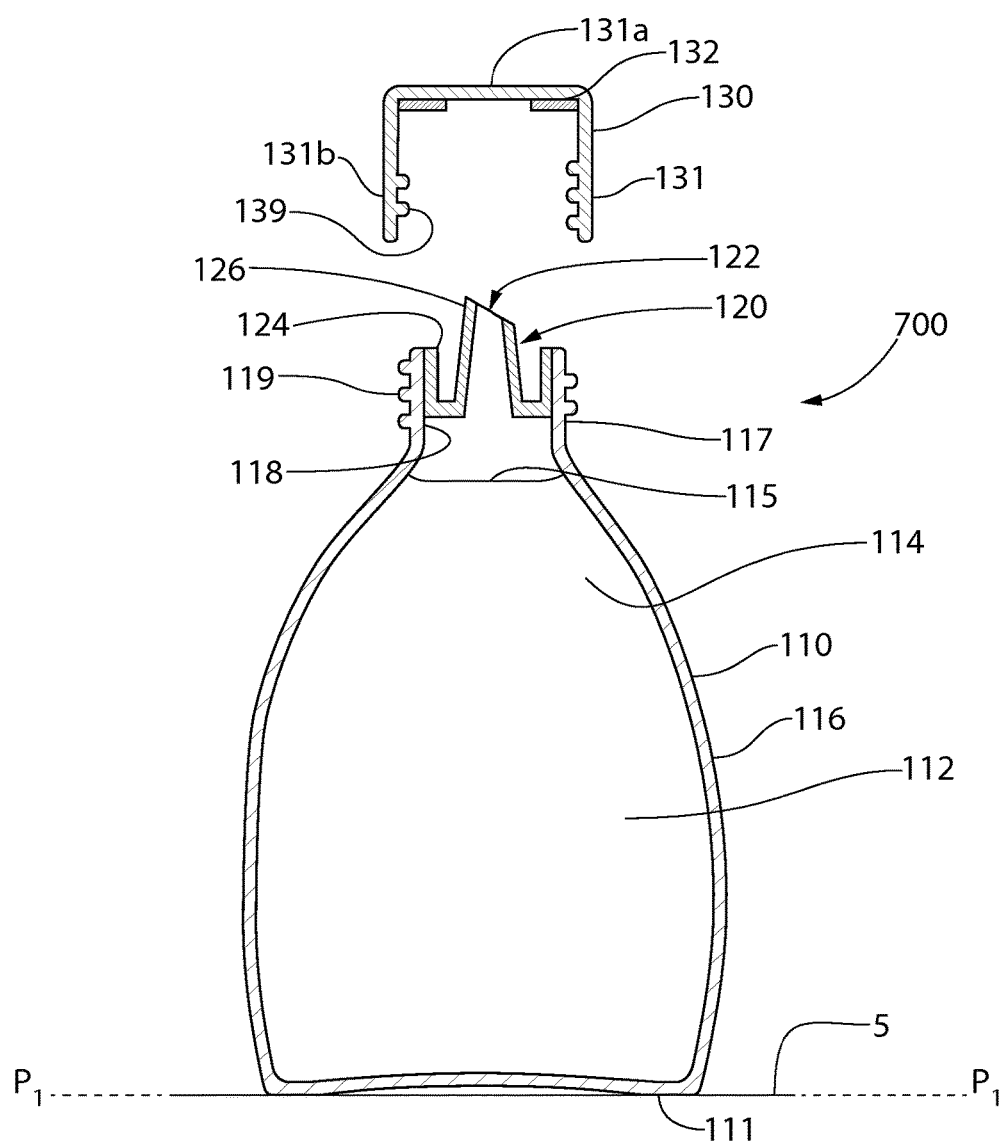
FIG. 7a shows a cross-sectional view of a container according to a further embodiment of the present invention with a closure thereof at a second position relative to a vessel thereof.
Figure 7B:
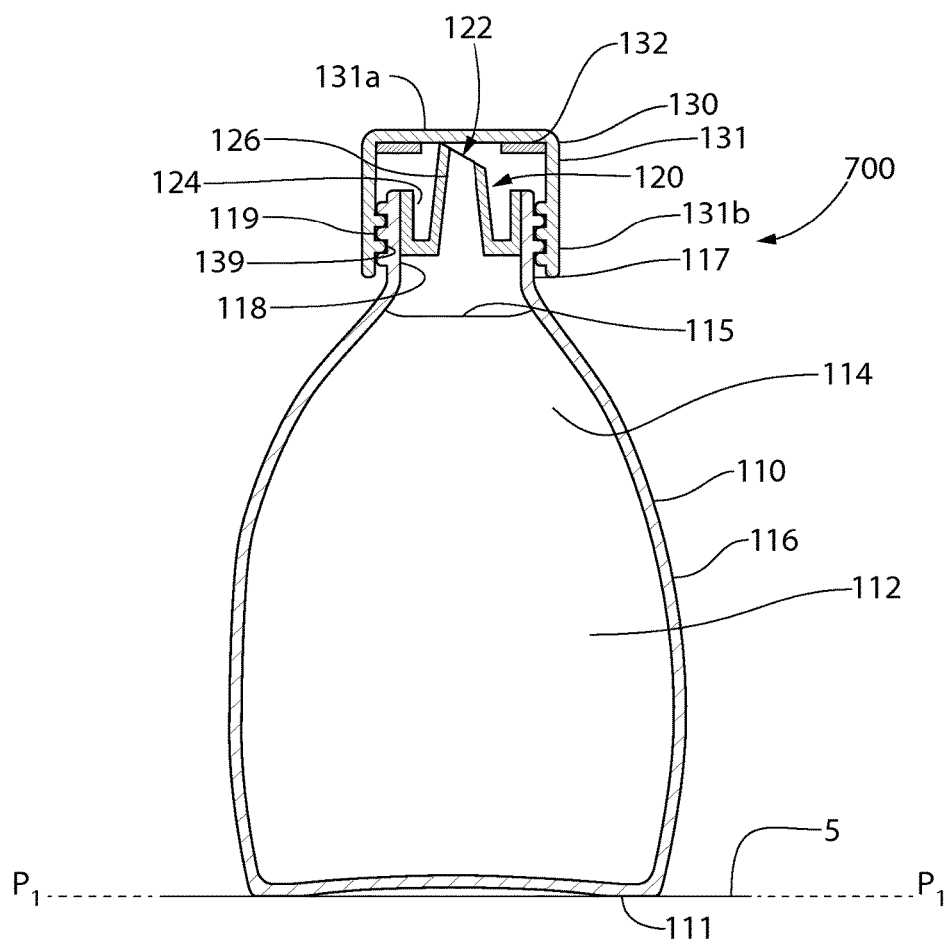
FIG. 7b shows a cross-sectional view of the container of FIG. 7a with the closure thereof at a first position relative to the vessel.

Another embodiment of a container of the present invention is shown in FIGS. 7a and 7b. Like elements in FIGS. 6a, 6b, 7a and 7b have like reference numerals and will not be described again for conciseness. Any of the above-described possible variations to the preceding described containers may be made to the container of FIGS. 7a and 7b.

The container 700 of FIGS. 7a and 7b differs from the container 600 of FIGS. 6a and 6b only in the location of the porous element for retaining a quantity of the flowable substance 114. The closure 130 of the container 700 of FIGS. 7a and 7b comprises a closure member 131 of the same form as the closure member 131 of the container 600 of FIGS. 6a and 6b, and the porous element 132 again is affixed to the closure member 131, preferably by adhesive. In a variation to this embodiment, the porous element 132 is unitary with the closure member 131. The porous element 132 is an annular element affixed to the floor 131a of the closure member 131 so that the skirt 131b surrounds the porous element 132.

The closure 130 is movable relative to the vessel 110 between a first position (see FIG. 7b) at which the closure 130 isolates the opening 122 from an exterior of the container 700 but the opening 122 is in fluid communication with the porous element 132, and a second position (see FIG. 7a) at which the opening 122 is in fluid communication with the exterior of the container 700 and the porous element 132. In a variation to the illustrated embodiment, the body 120 and closure 130 are relatively shaped so that, when the closure 130 is at the first position relative to the vessel 110, the porous element 132 is isolated from the opening 122, the chamber 112 and the volume of flowable substance 114 therein. When the closure 130 is at the first position relative to the vessel 110, the porous element 132 fully surrounds the body 120. In a variation to the illustrated embodiment, the porous element 132 is not annular and may only partially surround the body 120. On the other hand, when the closure 130 is at the second position relative to the vessel 110, the porous element 132 is in fluid communication with the chamber 112 and the volume of flowable substance 114 therein, and with the exterior of the container 700.

When the container 700 of FIGS. 7a and 7b is in a storage state (see FIG. 7b) and the closure 130 is at its first position relative to the vessel 110, if the container 700 is tilted 180 degrees (i.e. is turned upside down) relative to the horizontal during transportation to a retailer, or when being put on a shelf in a retailer's shop or store, the flowable substance 114 comes into contact with the porous element 132. Thus, the porous element 132 would retain a quantity of the flowable substance 114. When the closure 130 is at its second position relative to the vessel 110, after a user has tilted the container 700 sufficiently relative to the horizontal to dispense the flowable substance 114 from the chamber 112 through the opening 122 and into the closure member 131, so as to measure out a volume of the flowable substance 114, some of the flowable substance 114 will come into contact with the porous element 132. Thus, again the porous element 132 would retain a quantity of the flowable substance 114. The user can then pour the measured volume of the flowable substance 114 from the closure member 131 into its desired destination. Thus, after some of the flowable substance 114 has been dispensed, a fragrance of the flowable substance 114 is delivered not only through the opening 122 from the volume of the flowable substance 114 within the chamber 112 but also from the porous element 132 of the closure 130. Thus, a user is able to sniff to determine accurately the fragrance of the flowable substance 114. When the closure 130 is subsequently returned to its first position relative to the vessel 110, the porous element 132 is again isolated from the exterior of the container 700.

It will be appreciated that, in the container 700 of FIGS. 7a and 7b, the porous element 132 is not at a position relative to the volume of the flowable substance 114 so that the flowable substance 114 comes into contact with the porous element 132 as the flowable substance 114 is dispensed from the chamber 112 through the opening 122. However, the porous element 132 is at a position relative to the volume of the flowable substance 114 so that the flowable substance 114 comes into contact with the porous element 132 as a result of the flowable substance 114 being dispensed from the chamber 112 through the opening 122.

Figure 8A:
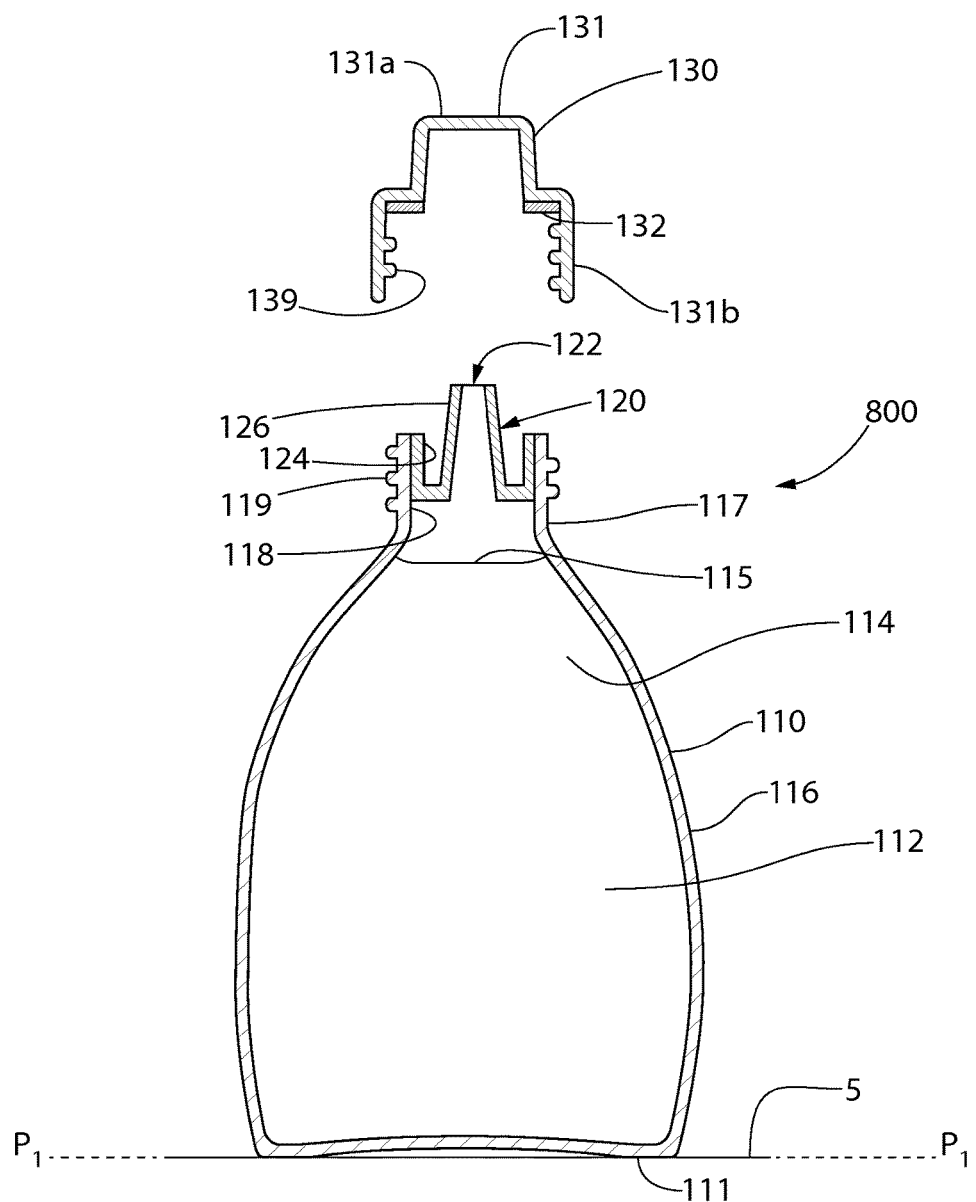
FIG. 8a shows a cross-sectional view of a container according to a further embodiment of the present invention with a closure thereof at a second position relative to a vessel thereof.
Figure 8B:
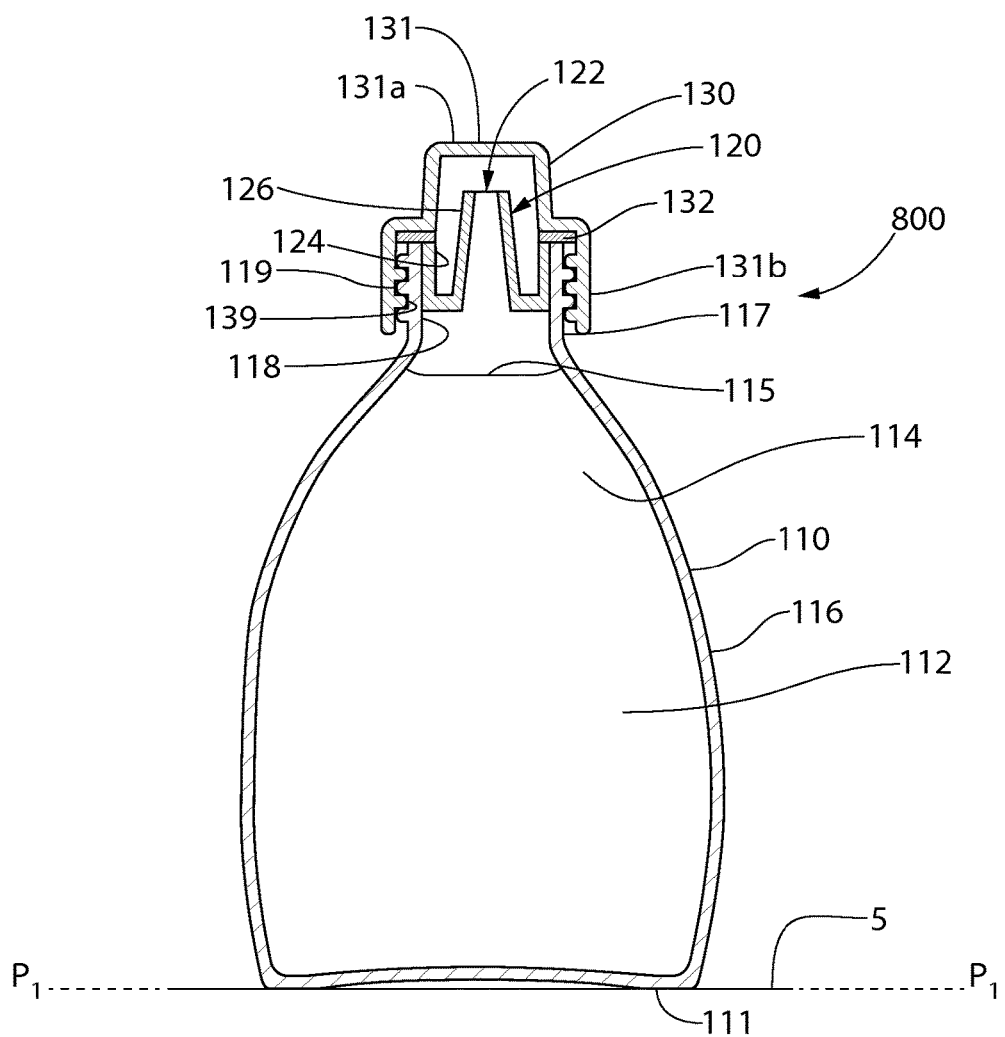
FIG. 8b shows a cross-sectional view of the container of FIG. 8a with the closure thereof at a first position relative to the vessel.

Another embodiment of a container of the present invention is shown in FIGS. 8a and 8b. Like elements in FIGS. 7a, 7b, 8a and 8b have like reference numerals and will not be described again for conciseness. Any of the above-described possible variations to the preceding described containers may be made to the container of FIGS. 8a and 8b.

The container 800 of FIGS. 8a and 8b differs from the container 700 of FIGS. 7a and 7b only in the form of the closure member 131 and the location of the porous element for retaining a quantity of the flowable substance 114. The closure member 131 of the container 800 of FIGS. 8a and 8b has a relatively narrow first portion, comprising the floor 131a and a first portion of the skirt 131b, and a relatively wide second portion comprising a second portion of the skirt 131b. The female screw thread 139 for mating with the male screw thread 119 at the exterior surface of the neck 117 of the vessel 110 is provided on an interior face of the second portion of the skirt 131b. The first portion of the closure member 131 is connected to an interior edge of an annular portion of the closure member 131, which annular portion is between the first and second portions of the closure member 131. The second portion of the closure member 131 is connected to an exterior edge of the annular portion of the closure member 131. The porous element 132 is an annular element affixed to the annular portion of the closure member 131, preferably by adhesive, so that the second portion of the skirt 131b surrounds the porous element 132. In a variation to this embodiment, the porous element 132 is unitary with the closure member 131.

The closure 130 is movable relative to the vessel 110 between a first position (see FIG. 8b) at which the closure 130 isolates the opening 122 from an exterior of the container 800, and a second position (see FIG. 8a) at which the opening 122 is not isolated from the exterior of the container 800 by the closure 130. When the closure 130 is at the first position relative to the vessel 110, the porous element 132 is in fluid communication with the chamber 112 and the volume of flowable substance 114 therein. Moreover, when the closure 130 is at the first position relative to the vessel 110, the porous element 132 is compressed between the closure 130 and one or both of the vessel 110 and the body 120, and the porous element 132 forms, or helps to form, a seal isolating an interior of the closure 130 from the exterior of the container 800. In a variation to the illustrated embodiment, the porous member 132 may not be compressed when the closure 130 is at the first position relative to the vessel 110. On the other hand, when the closure 130 is at the second position relative to the vessel 110, the porous element 132 is in fluid communication with the chamber 112, the volume of flowable substance 114 therein, and the exterior of the container 800. In a variation to the illustrated embodiment, when the closure 130 is at the first position relative to the vessel 110, the closure member 131 blocks the opening 122.

In FIG. 8b the container 800 is shown in a storage state with the base 111 of the vessel 110 in contact with the horizontal support surface 5 and the plane $P_1$-$P_1$ parallel to the horizontal support surface 5. In this storage state, although the porous element 132 is in fluid communication with the chamber 112 and the volume of the flowable substance 114 in the chamber 112, the porous element 132 is out of contact with the volume of the flowable substance 114 in the chamber 112. However, if the container 800 is tilted 180 degrees (i.e. is turned upside down) relative to the horizontal during transportation to a retailer, or when being put on a shelf in a retailer's shop or store, the flowable substance 114 comes into contact with the porous element 132, and the porous element 132 retains a quantity of the flowable substance 114. Accordingly, when a potential purchaser subsequently moves the closure 130 to its second position relative to the vessel 110 and sniffs to determine the fragrance of the flowable substance 114, the fragrance is delivered not only through the opening 122 from the volume of the flowable substance 114 within the chamber 112 but also from the porous element 132 of the closure 130. A potential purchaser is thus able to determine accurately the fragrance of the flowable substance 114 prior to purchase of the container 800.

It will be appreciated that, in the container 800 of FIGS. 8a and 8b, the porous element 132 is not at a position relative to the volume of the flowable substance 114 so that the flowable substance 114 comes into contact with the porous element 132 as the flowable substance 114 is dispensed from the chamber 112 through the opening 122. However, the porous element 132 is at a position relative to the volume of the flowable substance 114 so that the flowable substance 114 comes into contact with porous element 132 as a result of the flowable substance 114 being dispensed from the chamber 112 through the opening 122.

In respective variations to each of the embodiments of FIGS. 1 to 8b, one or more small apertures may be provided extending through the floor 131a and/or skirt 131b of the closure 130, each of which aperture(s) is in fluid communication with the porous element when the closure 130 is at the first position relative to the vessel 110. The, or each, of the apertures may define a flow path between the porous element and the exterior of the container, so that the fragrance of the flowable substance retained by the porous element is able to pass through the aperture(s) to the exterior of the container. The aperture(s) may for example be closer to the distal end of the skirt 131b than to the floor 131a, or may be in the floor 131a. In such respective variations to the illustrated embodiments, a removable seal may be provided on the exterior of the closure 130 so as to isolate the aperture(s) from the exterior of the container until such time as it is desired to smell the fragrance. The removable seal may be re-attachable to the closure 130 thereafter, so as to place the aperture(s) in fluid communication with the exterior of the container. That is, the seal may be on the exterior of the closure 130 and movable relative to the closure 130 between a first position at which the seal isolates the, or each, of the aperture(s) from the exterior of the container and a second position at which the seal does not isolate the, or each, of the aperture(s) from the exterior of the container.

Figure 9A:
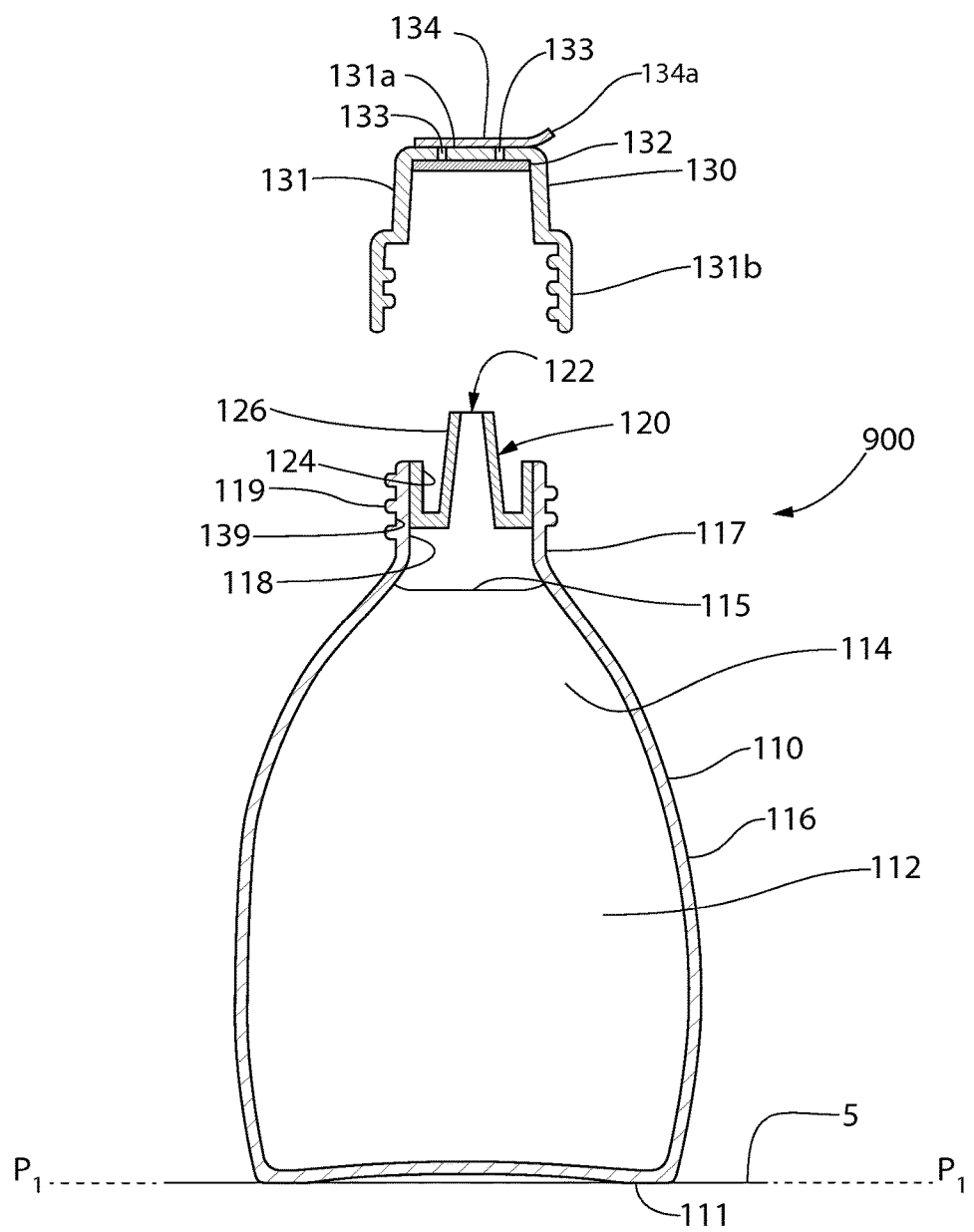
FIG. 9a shows a cross-sectional view of a container according to a further embodiment of the present invention with a closure thereof at a second position relative to a vessel thereof.
Figure 9B:
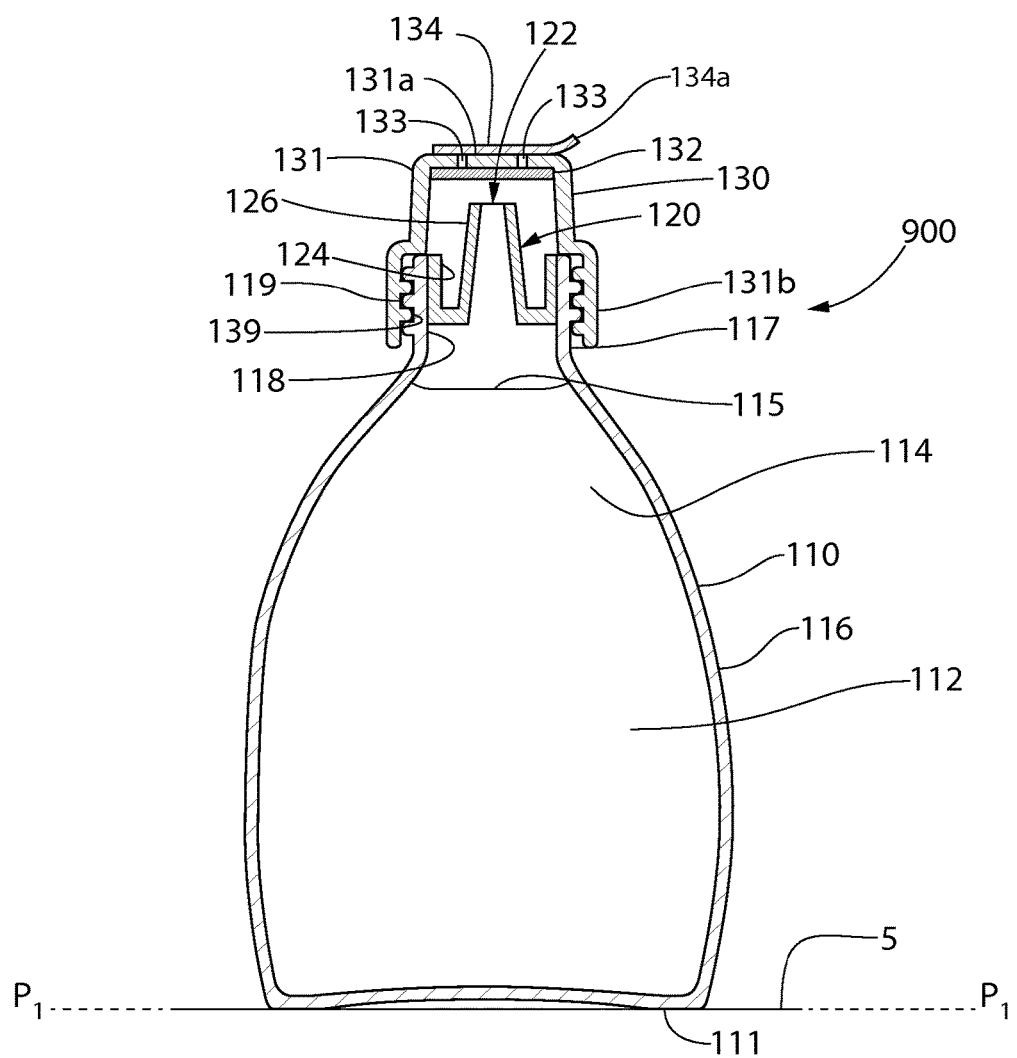
FIG. 9b shows a cross-sectional view of the container of FIG. 9a with the closure thereof at a first position relative to the vessel.

Another embodiment of a container of the present invention is shown in FIGS. 9a and 9b. Like elements in FIGS. 7a, 7b, 9a and 9b have like reference numerals and will not be described again for conciseness. Any of the above-described possible variations to the preceding described containers may be made to the container of FIGS. 9a and 9b.

The container 900 of FIGS. 9a and 9b differs from the container 700 of FIGS. 7a and 7b only in the form of the closure member 131 and the form of the porous element for retaining a quantity of the flowable substance 114. The closure member 131 of the container 900 of FIGS. 9a and 9b has a relatively narrow first portion, comprising the floor 131a and a first portion of the skirt 131b, and a relatively wide second portion comprising a second portion of the skirt 131b. The female screw thread 139 for mating with the male screw thread 119 at the exterior surface of the neck 117 of the vessel 110 is provided on an interior face of the second portion of the skirt 131b. The first portion of the closure member 131 is connected to an interior edge of an annular portion of the closure member 131, which annular portion is between the first and second portions of the closure member 131. The second portion of the closure member 131 is connected to an exterior edge of the annular portion of the closure member 131. The porous element 132 is a, preferably circular or disc-shaped, element affixed to the floor 131a of the closure member 131, preferably by adhesive, so that the second portion of the skirt 131b surrounds the porous element 132. In a variation to this embodiment, the porous element 132 is unitary with the closure member 131.

A plurality of apertures 133 extend through the floor 131a of the closure 130, each of which apertures 133 is in fluid communication with the porous element 132 when the closure 130 is at the first position relative to the vessel 110. A seal 134 is provided on the exterior of the closure 130 so as to isolate the apertures 133 from the exterior of the container 900 until such time as it is desired to smell the fragrance. The seal 134 is movable relative to the closure 130 between a first position (see FIG. 9b) at which the seal 134 isolates each of the apertures 133 from the exterior of the container 900 and a second position (not shown) at which the seal 134 does not isolate each of the apertures 133 from the exterior of the container 900. The seal 134 includes a handle portion 134a for facilitating a user's grip of the seal 134 when moving the seal 134 relative to the closure 130. In a variation to the illustrated embodiment, only one such aperture 133 is provided. In a variation to the illustrated embodiment, aperture(s) may instead or additionally extend through the skirt 131b of the closure 130, and optionally a removable seal may be provided to selectively isolate and un-isolate the aperture(s) that extend through the skirt 131b from the exterior of the container.

The closure 130 is movable relative to the vessel 110 between a first position (see FIG. 9b) at which the closure 130 isolates the opening 122 from an exterior of the container 900, and a second position (see FIG. 9a) at which the opening 122 is not isolated from the exterior of the container 900 by the closure 130. When the closure 130 is at the first position relative to the vessel 110, the porous element 132 is in fluid communication with the chamber 112 and the volume of flowable substance 114 therein. On the other hand, when the closure 130 is at the second position relative to the vessel 110, the porous element 132 is in fluid communication with the chamber 112, the volume of flowable substance 114 therein, and the exterior of the container 900. In a variation to the illustrated embodiment, in which the porous element 132 is annular, when the closure 130 is at the first position relative to the vessel 110 the closure member 131 blocks the opening 122.

In FIG. 9b the container 900 is shown in a storage state with the base 111 of the vessel 110 in contact with the horizontal support surface 5 and the plane $P_1$-$P_1$ parallel to the horizontal support surface 5. In this storage state, although the porous element 132 is in fluid communication with the chamber 112 and the volume of the flowable substance 114 in the chamber 112, the porous element 132 is out of contact with the volume of the flowable substance 114 in the chamber 112. However, if the container 900 is tilted 180 degrees (i.e. is turned upside down) relative to the horizontal during transportation to a retailer, or when being put on a shelf in a retailer's shop or store, the flowable substance 114 comes into contact with the porous element 132, and the porous element 132 retains a quantity of the flowable substance 114. Accordingly, when a potential purchaser subsequently moves the closure 130 to its second position relative to the vessel 110 and sniffs to determine the fragrance of the flowable substance 114, the fragrance is delivered not only through the opening 122 from the volume of the flowable substance 114 within the chamber 112 but also from the porous element 132 of the closure 130. A potential purchaser is thus able to determine accurately the fragrance of the flowable substance 114 prior to purchase of the container 900.

Improved delivery of the fragrance continues after a user has purchased the container 900. For example, when the container 900 is tilted sufficiently relative to the horizontal during transportation around the user's residence, the flowable substance 114 comes into contact with the porous element 132, and the porous element 132 retains a quantity of the flowable substance 114. Moreover, when the closure 130 is at its second position relative to the vessel 110, after a user has tilted the container 900 sufficiently relative to the horizontal to dispense the flowable substance 114 from the chamber 112 through the opening 122 and into the closure member 131, so as to measure out a volume of the flowable substance 114, some of the flowable substance 114 will come into contact with the porous element 132. Thus, the porous element 132 would retain a quantity of the flowable substance 114. The user can then pour the measured volume of the flowable substance 114 from the closure member 131 into its desired destination. Thus, after some of the flowable substance 114 has been dispensed, a fragrance of the flowable substance 114 is delivered not only through the opening 122 from the volume of the flowable substance 114 within the chamber 112 but also from the porous element 132 of the closure 130. Thus, a user is able to sniff to determine accurately the fragrance of the flowable substance 114.

It will be appreciated that, in the container 900 of FIGS. 9a and 9b, the porous element 132 is not at a position relative to the volume of the flowable substance 114 so that the flowable substance 114 comes into contact with the porous element 132 as the flowable substance 114 is dispensed from the chamber 112 through the opening 122. However, the porous element 132 is at a position relative to the volume of the flowable substance 114 so that the flowable substance 114 comes into contact with the porous element 132 as a result of the flowable substance 114 being dispensed from the chamber 112 through the opening 122.

In respective variations to each of the illustrated and above-described embodiments, the body may be shaped so that at least some of any of the flowable substance that runs down the radial outside surface of the body following dispensing can drain back into the into the chamber of the vessel. For example, the body may define a channel extending from the opening towards the vessel, and/or the body may have one or more holes extending therethrough in parallel to the opening and fluidly connecting the chamber with the radial outside surface of the body. Such a channel or hole(s) could act as a vent to permit air to enter the chamber during dispensing of the flowable substance through the opening, in order to avoid the build-up of negative pressure in the chamber and/or chugging of the flowable substance during dispensing of the flowable substance.

In each of the illustrated embodiments the flowable substance is a home care product, more specifically a fabric conditioner. However, in respective variations to the illustrated embodiments, the flowable substance is a different home care product, such as one of a laundry detergent, a dish washing detergent, a fabric softener, a floor cleaner, and a surface cleaner. In other respective variations to the illustrated embodiments, the flowable substance is a personal care product, such as one of a hand soap, a dentifrice, a hair care product, a body wash, and a mouthwash.

While not shown, in variations to each of the embodiments as described above, the spout 126 may include a flared section in which the transverse width of the spout 126 increases from one end close to the opening 122 to the other end where the flowable substance 114 leaves the container 100. The increase in the transverse width results in an increase in the contact surface area between the spout 126 and the flowable substance 114. In other embodiments, the spout 126 may include one or more topographical features, such as ribs, ridges, protrusions, protuberances, troughs, gaps, voids, etc. The topographical features may help to increase the contact surface area between the spout 126 and the flowable substance 114 and/or alter the fluid dynamic of the flowable substance 114 as the flowable substance 114 leaves the container 100. It is understood that the increase in the contact surface area between the spout 126 and the flowable substance 114 helps to increase the release of the fragrance of the flowable substance 114.

Other modifications and embodiments of the present invention will be apparent to those skilled in the art.

What is claimed is:

1. A container, comprising:
    a vessel defining a chamber for storing a volume of a flowable substance having a fragrance;
    a body defining an opening through which the flowable substance is dispensable from the chamber; and
    a closure movable removably attached to the vessel and movable relative to the vessel between a first position at which the closure is attached to the vessel and isolates the opening from an exterior of the container and a second position at which the closure is removed from the vessel such that the opening is not isolated from the exterior of the container by the closure, the closure comprising a porous element for retaining a quantity of the flowable substance.

2. The container of claim 1, wherein the closure comprises a closure member, and wherein the porous element is affixed to the closure member or is unitary with the closure member.

3. The container of claim 1, wherein the closure is movable relative to the vessel between the first position at which at least a portion of the porous member is in the opening and the second position at which none of the porous member is in the opening.

4. The container of claim 1, wherein the porous element forms a seal isolating an interior of the closure from an exterior of the container when the closure is at the first position relative to the vessel.

5. The container of claim 1, wherein the porous element is compressed between the closure and one of the body and the vessel when the closure is at the first position relative to the vessel.

6. The container of claim 1, wherein the porous element is in fluid communication with the chamber when the closure is at the first position relative to the vessel.

7. The container of claim 1, wherein the porous element is isolated from an exterior of the container when the closure is at the first position, and wherein the porous element is in fluid communication with the exterior of the container when the closure is at the second position.

8. The container of claim 1, wherein the porous element partially or fully surrounds the body when the closure is at the first position.

9. The container of claim 1, wherein one or more apertures extend through the closure, each of the one or more apertures being in fluid communication with the porous element when the closure is at the first position relative to the vessel.

10. The container of claim 9, comprising a seal on the exterior of the closure, wherein the seal is movable relative to the closure between a first position at which the seal isolates the, or each, of the one or more apertures from an exterior of the container and a second position at which the seal does not isolate the, or each, of the one or more apertures from the exterior of the container.

11. The container of claim 1, wherein the opening is defined by a spout.

12. The container of claim 1, wherein the porous element comprises one or more of a wick, sintered plastic, pulp material, screen material, and pressed paperboard.

13. The container of claim 1, wherein the flowable substance is one of a personal care product and a home care product; optionally wherein the personal care product is one of a hand soap, a dentifrice, a hair care product, a body wash, and a mouthwash, or wherein the home care product is one of a laundry detergent, a dish washing detergent, a fabric softener, a fabric conditioner, a floor cleaner, and a surface cleaner.

* * * * *